US012661242B2

(12) United States Patent
Taszreak et al.

(10) Patent No.: US 12,661,242 B2
(45) Date of Patent: Jun. 23, 2026

(54) HYDRAULIC PROSTHETIC ANKLE

(71) Applicant: College Park Industries, Inc., Warren, MI (US)

(72) Inventors: Aaron John Taszreak, Warren, MI (US); Jacob Michael Drews, Washington, MI (US); Anna Mae Marlatt, Waterford, MI (US); Kevin L'Heureux, Lincoln Park, MI (US)

(73) Assignee: College Park Industries, Inc., Warren, MI (US)

( * ) Notice: Subject to any disclaimer, the term of this patent is extended or adjusted under 35 U.S.C. 154(b) by 1073 days.

(21) Appl. No.: 17/663,751

(22) Filed: May 17, 2022

(65) Prior Publication Data

US 2022/0370212 A1 Nov. 24, 2022

Related U.S. Application Data

(60) Provisional application No. 63/190,160, filed on May 18, 2021.

(51) Int. Cl.
*A61F 2/66* (2006.01)
*A61F 2/74* (2006.01)

(52) U.S. Cl.
CPC ............ *A61F 2/6607* (2013.01); *A61F 2/748* (2021.08)

(58) Field of Classification Search
CPC .. A61F 2/6607; A61F 2/70; A61F 2/74; A61F 2/748
See application file for complete search history.

(56) References Cited

U.S. PATENT DOCUMENTS

| | | | |
|---|---|---|---|
| 6,719,807 B2 | 4/2004 | Harris | |
| 6,805,717 B2 | 10/2004 | Christensen | |
| 6,966,933 B2 | 11/2005 | Christensen | |
| 7,393,364 B2 | 7/2008 | Martin | |
| 7,985,265 B2 | 7/2011 | Moser et al. | |

(Continued)

FOREIGN PATENT DOCUMENTS

| | | | |
|---|---|---|---|
| EP | 2 726 022 | | 12/2020 |
| JP | 2014221093 A | * | 11/2014 |

(Continued)

OTHER PUBLICATIONS

Translation of JP2014221093A (Year: 2014).*

(Continued)

*Primary Examiner* — Christie Bahena

(74) *Attorney, Agent, or Firm* — Knobbe, Martens, Olson & Bear, LLP

(57) ABSTRACT

A prosthetic ankle device is disclosed herein. The prosthetic ankle device includes a hydraulic cylinder with a first chamber, a second chamber, and a piston separating the first chamber and the second chamber. The chambers are filled with hydraulic fluid. During plantarflexion, the hydraulic fluid flows between the first chamber and the second chamber via a first passage and a first check valve. During dorsiflexion, the hydraulic fluid flows between the first chamber and the second chamber via a second passage and a second check valve. The ankle device includes a third passage and a third check valve, where the third passage diverts flow of the hydraulic fluid from the second passage based at least in part on a system status.

16 Claims, 18 Drawing Sheets

(56) References Cited

U.S. PATENT DOCUMENTS

| | | | |
|---|---|---|---|
| 8,574,312 | B2 | 11/2013 | Moser et al. |
| 8,628,585 | B2 | 1/2014 | Harris et al. |
| 8,641,780 | B2 | 2/2014 | Abimosleh et al. |
| 8,728,171 | B2 | 5/2014 | Kaltenborn et al. |
| 8,740,991 | B2 | 6/2014 | Moser et al. |
| 8,974,543 | B2 | 3/2015 | Balboni et al. |
| 8,986,398 | B2 | 3/2015 | Poulson, III et al. |
| 9,028,557 | B2 | 5/2015 | Steele et al. |
| 9,066,819 | B2 | 6/2015 | Gramnaes |
| 9,114,029 | B2 | 8/2015 | Asgeirsson et al. |
| 9,132,023 | B2 | 9/2015 | Moser et al. |
| 9,161,846 | B2 | 10/2015 | Mosler |
| 9,433,513 | B2 | 9/2016 | Moser et al. |
| 9,717,606 | B2 | 8/2017 | Gramnaes |
| 9,763,809 | B2 | 9/2017 | Palmer et al. |
| 9,820,871 | B2 | 11/2017 | Arabian et al. |
| 9,999,526 | B2 | 6/2018 | Moser et al. |
| 10,039,652 | B2 | 8/2018 | Zahedi et al. |
| 10,130,495 | B2 | 11/2018 | Moser et al. |
| 10,226,361 | B2 | 3/2019 | Mooney et al. |
| 10,285,827 | B2 | 5/2019 | Zahedi et al. |
| 10,314,724 | B2 | 6/2019 | Arabian et al. |
| 10,335,291 | B2 | 7/2019 | Bonnet et al. |
| 10,406,001 | B2 | 9/2019 | Harris et al. |
| 10,687,965 | B2 | 6/2020 | Palmer et al. |
| 10,702,403 | B2 | 7/2020 | Lincoln et al. |
| 10,758,376 | B2 | 9/2020 | Kaltenborn et al. |
| 2002/0138153 | A1 | 9/2002 | Koniuk |
| 2009/0030530 | A1 | 1/2009 | Martin |
| 2009/0222105 | A1 | 9/2009 | Clausen |
| 2014/0249652 | A1* | 9/2014 | Taszreak ............... A61F 2/6607 623/50 |
| 2018/0008434 | A1 | 1/2018 | Geiger et al. |
| 2018/0036148 | A1 | 2/2018 | Lincoln et al. |
| 2019/0254844 | A1 | 8/2019 | Hansen et al. |
| 2021/0015638 | A1 | 1/2021 | Taszreak et al. |
| 2021/0106441 | A1 | 4/2021 | Naseri et al. |
| 2023/0083387 | A1 | 3/2023 | Taszreak et al. |

FOREIGN PATENT DOCUMENTS

| | | | |
|---|---|---|---|
| WO | WO-2014005679 A2 * | 1/2014 | ............... A61H 3/00 |
| WO | WO 2022/245743 | 11/2022 | |

OTHER PUBLICATIONS

International Search Report and Written Opinion received in PCT Application No. PCT/US2022/029472 dated Aug. 22, 2022 in 11 pages.
International Preliminary Report on Patentability and Written Opinion received in PCT Application No. PCT/US2022/029472 dated Nov. 30, 2023 in 8 pages.

* cited by examiner

700

702 — Begin

704 — Is a first condition satisfied?

No

Yes

706 — Change diverter position from a position to a second position

708 — Wait

710 — Is a second condition satisfied?

No

Yes

712 — Change diverter position from the second position to the first position

HYDRAULIC PROSTHETIC ANKLE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure is related to prosthetic or orthotic systems, in particular to systems and methods controlling a relative position or movement between a foot portion and an ankle portion of a prosthetic or an orthotic device by controlling hydraulic fluid flow.

Description of the Related Art

Relative positions or movements between a foot portion and an ankle portion of a prosthetic device or an orthotic device during gait may be controlled to assist smooth transition between different stages of the gait cycle. For example, a system may be implemented to prevent or reduce the likelihood of a prosthetic device or an orthotic device accidentally dragging against the ground during the swing phase of the gait cycle.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices, and methods for facilitating plantarflexion and dorsiflexion during the gait cycle.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

In accordance to one aspect, a prosthetic ankle is disclosed. The prosthetic ankle can include a hydraulic cylinder, a first valve, a second valve, a third valve, and a diverter valve. The hydraulic cylinder includes a first chamber, a second chamber, and a piston separating the first chamber and second chamber. The first and second chambers are filled with hydraulic fluid. The first valve is disposed along a first passage, the first passage and first valve allowing dampened fluid flow between the first and second chambers during plantarflexion. The second valve is disposed along a second passage, the second passage and second valve allowing dampened fluid flow between the first and second chambers during dorsiflexion. The diverter valve is in selective communication with the second passage and a third passage. The third valve is disposed along the third passage, the third passage and third valve allowing flow between the first and second chambers during dorsiflexion in a swing phase of gait. The dampening on the flow through the third passage is lower than the dampening on the flow through the second passage. The diverter valve diverts the flow from the second passage to the third passage based on a system status.

Various embodiments of the various aspects described herein may be implemented. The prosthetic ankle may include a spring disposed in the hydraulic cylinder and operatively coupled to the piston. The spring may impart a force on the piston during swing phase to dorsiflex a prosthetic foot coupled to the prosthetic ankle to lift a toe of the foot. The third passage and third check valve may allow non-restrictive flow between the first and second chambers. The system status may include a sensed pressure amount or rate of change. The system status may include a degree of dorsiflexion. The system status may include an indication of toe off.

In accordance to another aspect, a prosthetic device is disclosed. The prosthetic device includes a foot portion and an ankle portion coupled to the foot portion. The ankle portion includes a hydraulic cylinder, a first valve, a check valve, a third valve, and a diverter valve. The hydraulic cylinder includes a first chamber, a second chamber, and a piston separating the first chamber and second chamber, the first and second chambers filled with hydraulic fluid. The first valve is disposed along a first passage, the first passage and first valve allowing dampened fluid flow between the first and second chambers during plantarflexion. The second valve is disposed along a second passage, the second passage and second valve allowing dampened fluid flow between the first and second chambers during dorsiflexion. The diverter valve is in communication with the second passage and a third passage. The third valve is disposed along the third passage, the third passage and third valve allowing flow between the first and second chambers during dorsiflexion in a swing phase of gait. The dampening on the flow through the third passage is lower than the dampening on the flow through the second passage. The diverter valve diverts the flow from the second passage to the third passage based on a system status. An orientation of a top portion of the ankle portion changes based at least in part on a position of the piston within the hydraulic cylinder.

Various embodiments of the various aspects described herein may be implemented. The prosthetic device may include a spring disposed in the hydraulic cylinder and coupled to the piston. The spring may impart a force on the piston during swing phase to dorsiflex a prosthetic foot coupled to the prosthetic ankle to lift a toe of the foot during swing. The third passage and third check valve may allow non-restrictive flow between the first and second cylinder. The system status may include a pressure amount or rate of change. The system status may include a degree of dorsiflexion. The system status may include an indication of toe off.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

Figure 1:
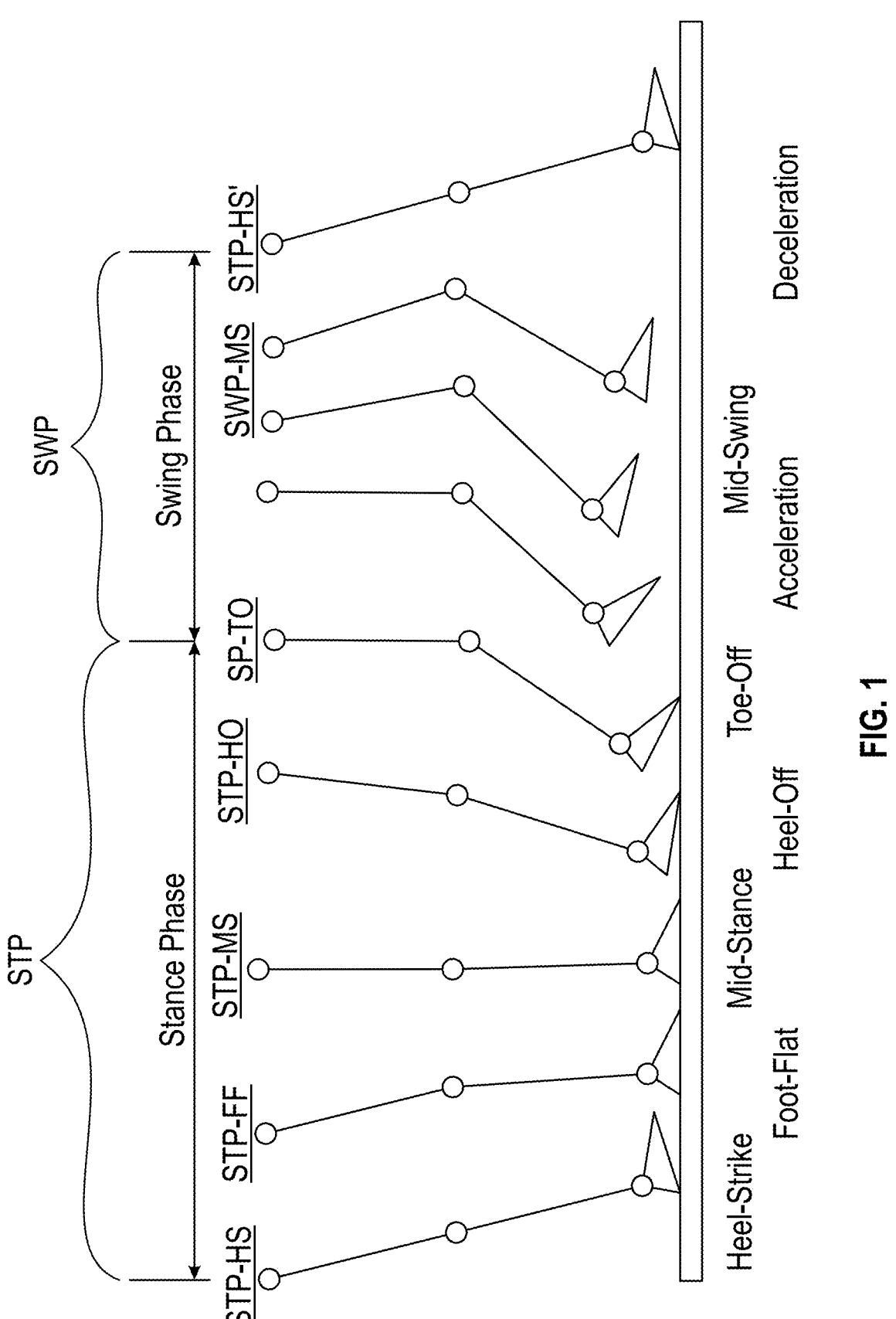
FIG. 1 illustrates different phases of the gait cycle.

The foregoing and other features of the present development will become more fully apparent from the following description and appended claims, taken in conjunction with the accompanying drawings. Understanding that these drawings depict only several embodiments in accordance with the development and are not to be considered limiting of its scope, the development will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present development, as generally described herein, and illustrated in the drawings, can be arranged, substituted, combined, and designed in a wide variety of different configurations, all of which are explicitly contemplated and make part of this disclosure.

DETAILED DESCRIPTION

Although certain embodiments and examples are described herein, this disclosure extends beyond the specifically disclosed embodiments and/or uses and obvious modifications and equivalents thereof. Thus, it is intended that the scope of this disclosure should not be limited by any particular embodiments described below.

FIG. 1 illustrates different phases of the gait cycle. The gait cycle can be divided into two different phases: a stance phase and a swing phase. Both the stance phase and the swing phase can include a number of stages. The stance phase can include heel-strike (HS), foot-flat (FF), mid-stance (MS), heel-off (HO), and toe-off (TO). The stance phase may begin with heel-strike (HS) and end with toe-off (TO) as shown in FIG. 1. After toe-off (TO), the swing phase can begin. The swing phase can extend between toe-off (TO), through mid-swing (MS), and end at heel-strike (HS) as shown in FIG. 1. After heel-strike (HS), the gait cycle can repeat with another set of the stance phase and the swing phase.

During the stance phase, a foot can undergo dorsiflexion and plantarflexion. A foot undergoes plantarflexion between heel-strike (HS) and mid-stance (MS), and dorsiflexion between mid-stance (MS) and toe-off (TO). For prosthetic devices such as a prosthetic foot shown in FIG. 2, a toe portion of the prosthetic foot can drop (or undergo plantarflexion) during the swing phase and cause the prosthetic foot to drag. As such, it is advantageous to have a system that can facilitate the prosthetic device to maintain dorsiflexion or reach its maximum-dorsiflexion position (i.e., lift the toe of the foot) during the swing phase to prevent or reduce the likelihood of dragging of the prosthetic foot, which may cause the user to trip.

Figure 2:
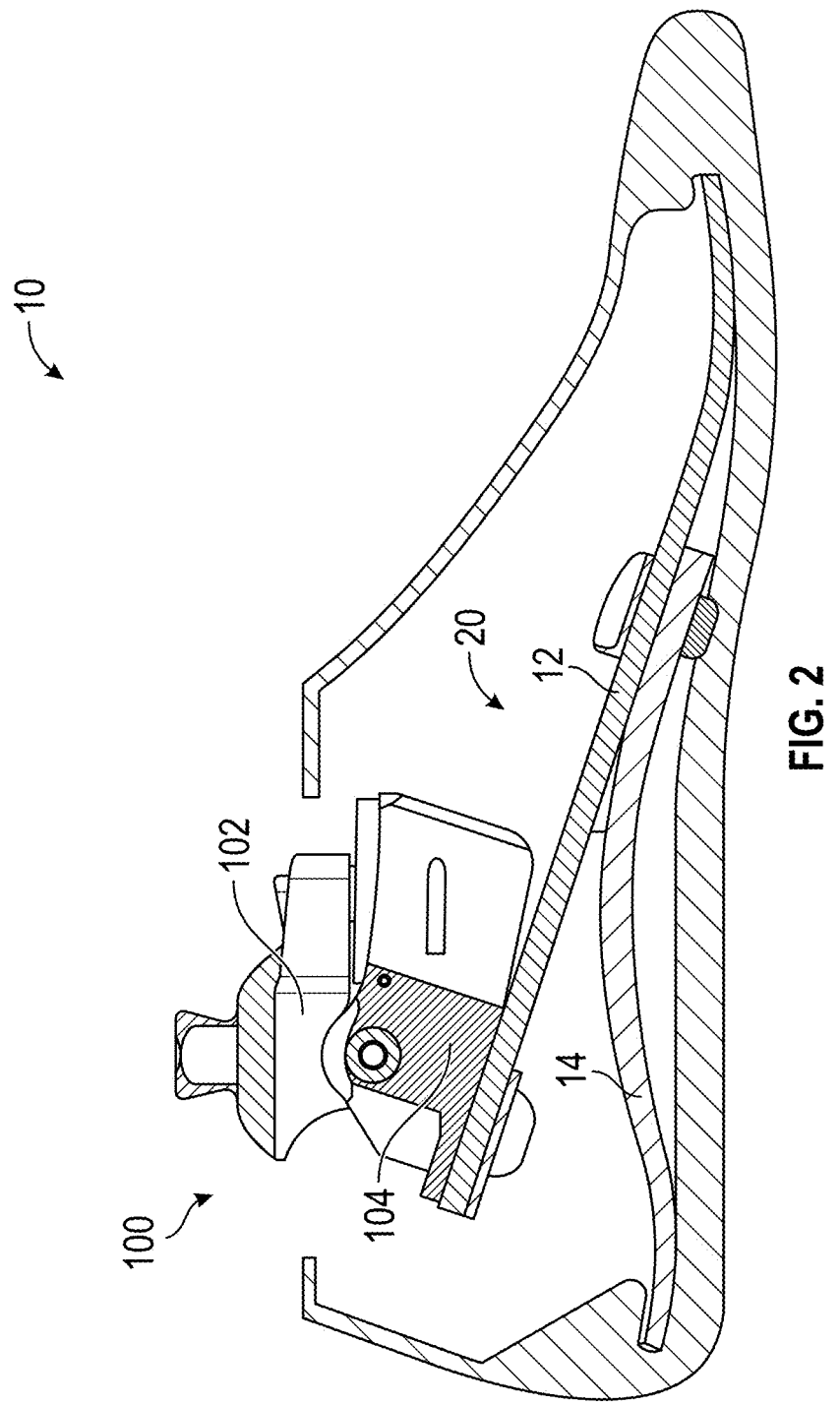
FIG. 2 illustrates a schematic partial cross-sectional view of an embodiment of a prosthetic or an orthotic device with a hydraulic prosthetic ankle.
Figure 3:
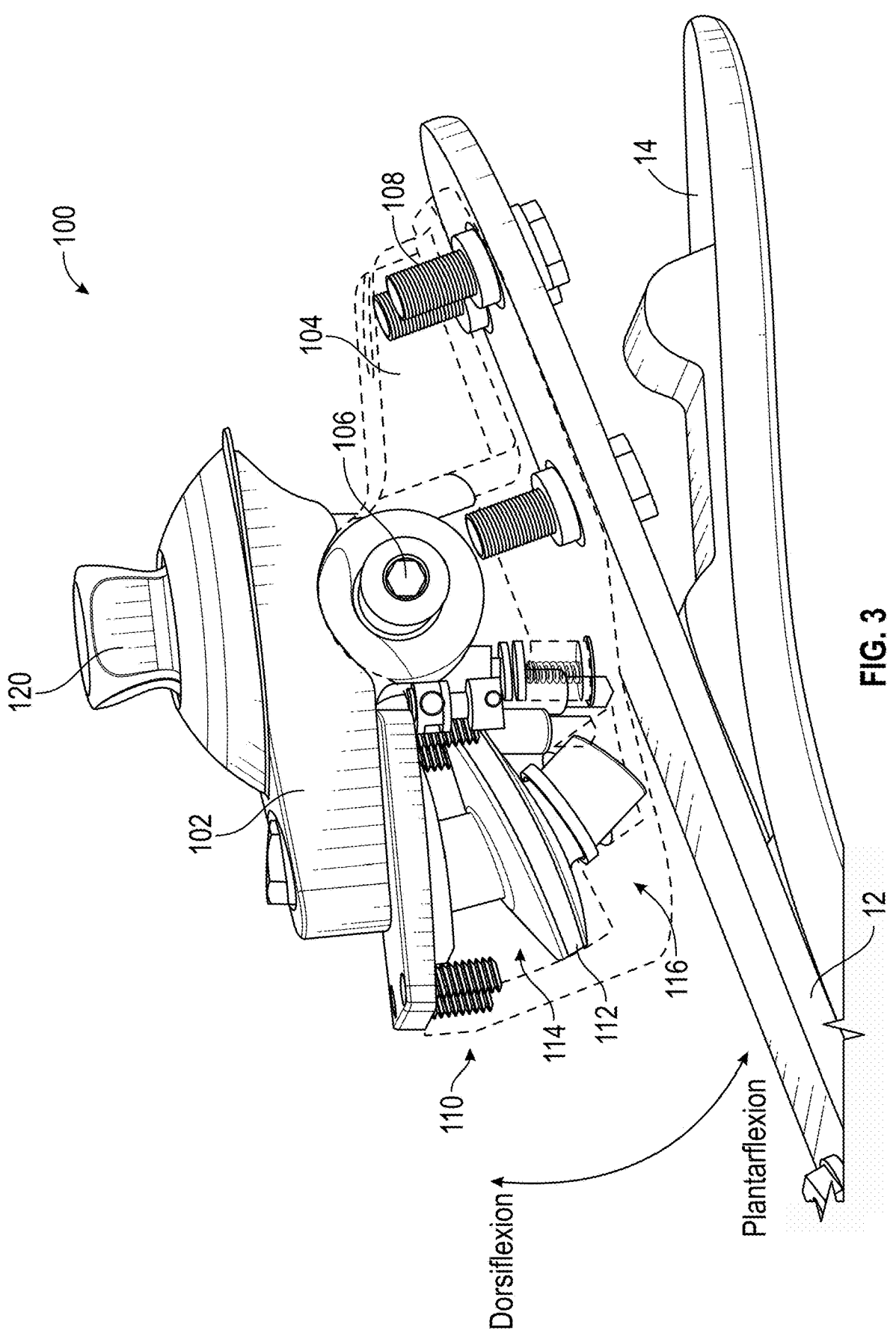
FIG. 3 illustrates a perspective view of the prosthetic or the orthotic device of FIG. 2, showing details of various components.

With references to FIGS. 2 and 3, a prosthetic device 10 (e.g., a prosthetic foot) can include a hydraulic prosthetic ankle 100 and a foot portion 20. The foot portion 20 can include a top plate 12, and a heel plate 14. The hydraulic prosthetic ankle 100 can include a top portion 102 and a bottom portion 104 that are rotatably coupled via an axle 106. The bottom portion 104 can be coupled to the top plate 12 of the foot portion 20 using, for example, one or more fasteners (e.g., bolts, screws) 108 such that movement of, for example, the bottom portion 104 translates to foot portion 20. For example, angular displacement of the bottom portion 104 with respect to the top portion 102 (e.g., plantarflexion or moving downward and away from the top portion 102) can cause the foot portion 20 to undergo angular displacement with respect to the top portion 102. Other suitable devices or connectors may be used to couple the bottom portion 104 of the hydraulic prosthetic ankle 100 with the top plate 12. The top plate 12 can be coupled to a heel plate 14 with one or more fasteners (e.g., bolts, screws). The heel plate 14 can extend rearward to a free end. In some implementations, the heel plate 14 can include an arch as shown in FIG. 2. The top portion 102 can be used to couple the prosthetic device 10 to a user's limb (e.g., a calf).

The hydraulic prosthetic ankle 100 can include a hydraulic cylinder 110. The hydraulic cylinder 110 can include a piston 112, a first chamber 114, and a second chamber 116. In some implementations, the hydraulic cylinder 110 is defined within the bottom portion 104 and the piston 112 is coupled to the top portion 102. The piston 112 can move within the hydraulic cylinder 110 to reflect the change in the angular position or orientation of the bottom portion 104 (or the top plate 12) with respect to the top portion 102. The top portion 102 can have an adapter 120, for connecting another prosthetic component (e.g., pylon). In one implementation, the adapter 120 can be a pyramid connector.

The first chamber 114 can be the space within the hydraulic cylinder 110 between a bottom end (for example, an end of the hydraulic cylinder 110 proximate to the top plate 12)

of the hydraulic cylinder 110 and the piston 112. The second chamber 116 can be the space within the hydraulic cylinder 110 between a top end (for example, an end of the hydraulic cylinder 110 proximate to the top portion 102) of the hydraulic cylinder 110 and the piston 112.

The position of the piston 112 within the hydraulic cylinder 110 can correspond to the angular displacement or the orientation of the foot portion 20 (or the bottom portion 104) with respect to the top portion 102. Likewise, the movement of the piston 112 within the hydraulic cylinder 110 can correspond to the movement of the foot portion 20 (or the bottom portion 104) with respect to the top portion 102. During dorsiflexion, the foot portion 20 can move upwards towards the top portion 102. The upward movement of the foot portion 20 can cause the piston 112 to move, for example, downward towards the bottom end of the hydraulic cylinder 110. During plantarflexion, the foot portion 20 can move downwards and away from the top portion 102. The downward movement of the foot portion 20 can cause the piston 112 to move, for example, upward towards the top end of the hydraulic cylinder 110.

The hydraulic cylinder 110 can contain hydraulic fluid that can flow between the first chamber 114 and the second chamber 116 via a number of passages. As discussed herein, the movement of the foot portion 20 can cause, for example, movement of the piston 112 with respect to the hydraulic cylinder 110, which can cause the hydraulic fluid to flow between the first chamber 114 and the second chamber 116. In some implementations, contact between the inner sidewalls of the hydraulic cylinder 110 and the piston 112 (e.g., a seal attached to the piston) can inhibit (e.g., prevent) direct flow of the hydraulic fluid between the first chamber 114 and the second chamber 116 (for example, bypassing the passages as described herein).

Figure 4A:
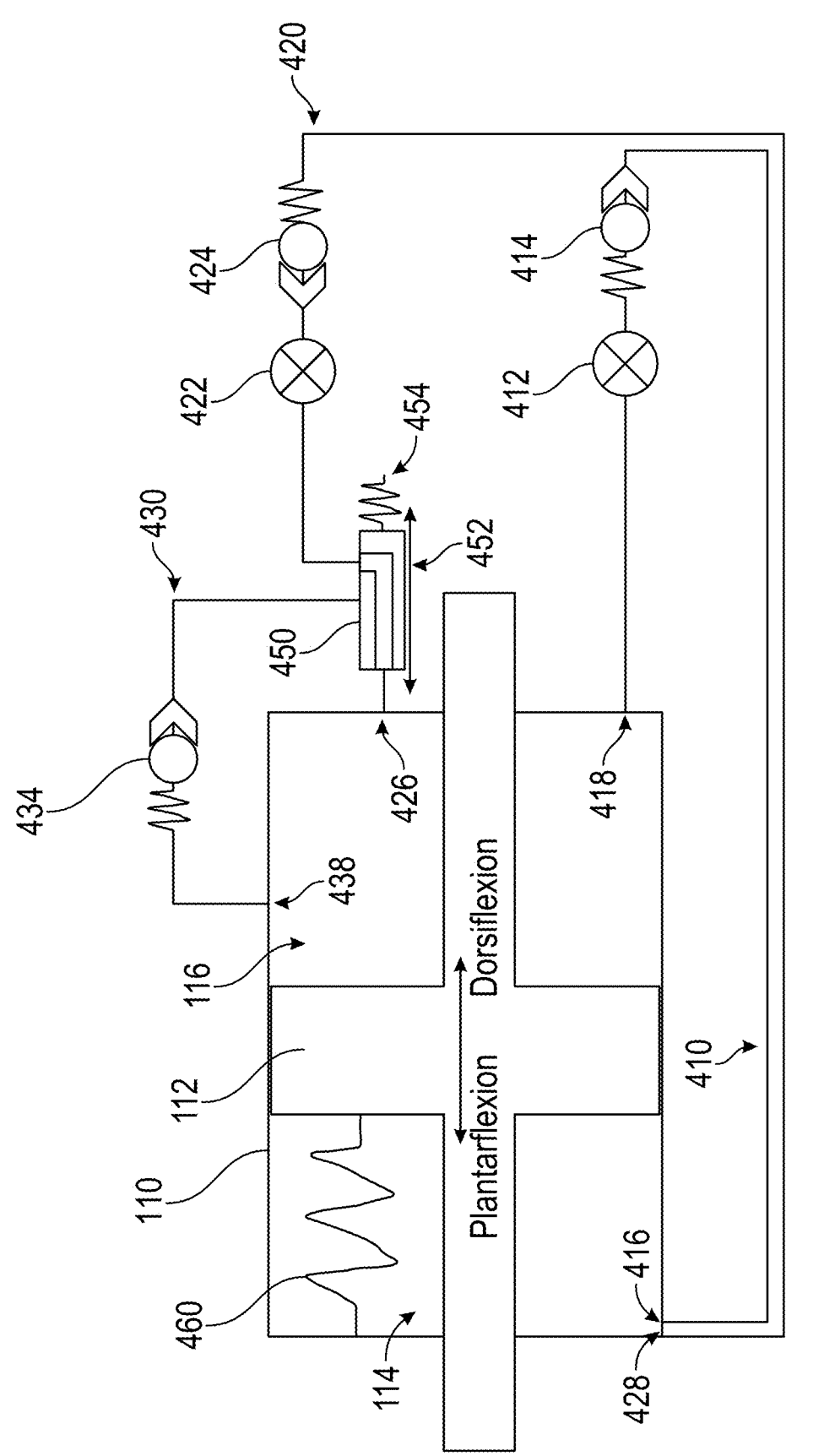
FIGS. 4A-4D schematically illustrate operation of an embodiment of a hydraulic prosthetic ankle during different phases of gait.

FIG. 4A schematically illustrates various components of a hydraulic system 400 of the hydraulic prosthetic ankle 100. In the example illustrated in FIG. 4A, the hydraulic system 400 can include the hydraulic cylinder 110, the piston 112, the first chamber 114, and the second chamber 116 as described herein. In addition, the hydraulic system 400 can include a first passage 410, a second passage 420, a third passage 430, and a diverter valve 450. The components of the hydraulic system 400 can control the flow of hydraulic fluid within the hydraulic system 400 to provide improved control of the relative angular positions or movements of the top portion 102 and the bottom portion 104 during gait.

The first passage 410 can include a first valve 412, a first check valve 414, and openings 416, 418 via which the first passage 410 communicates with the first chamber 114 and second chamber 116, respectively. The first valve 412 is selectively adjustable to adjust a hydraulic damping resistance within the hydraulic system 400. For example, the first valve 412 can restrict the flow of hydraulic fluid through the first passage 410 (e.g., by adjusting a size of an orifice in the valve through which hydraulic fluid flows), which can generate hydraulic resistance against the movement of the piston 112. In some implementations, the hydraulic dampening resistance generated by the first valve 412 can be varied by adjusting, for example, position, orientation, or configuration of the first valve 412.

Figure 4B:
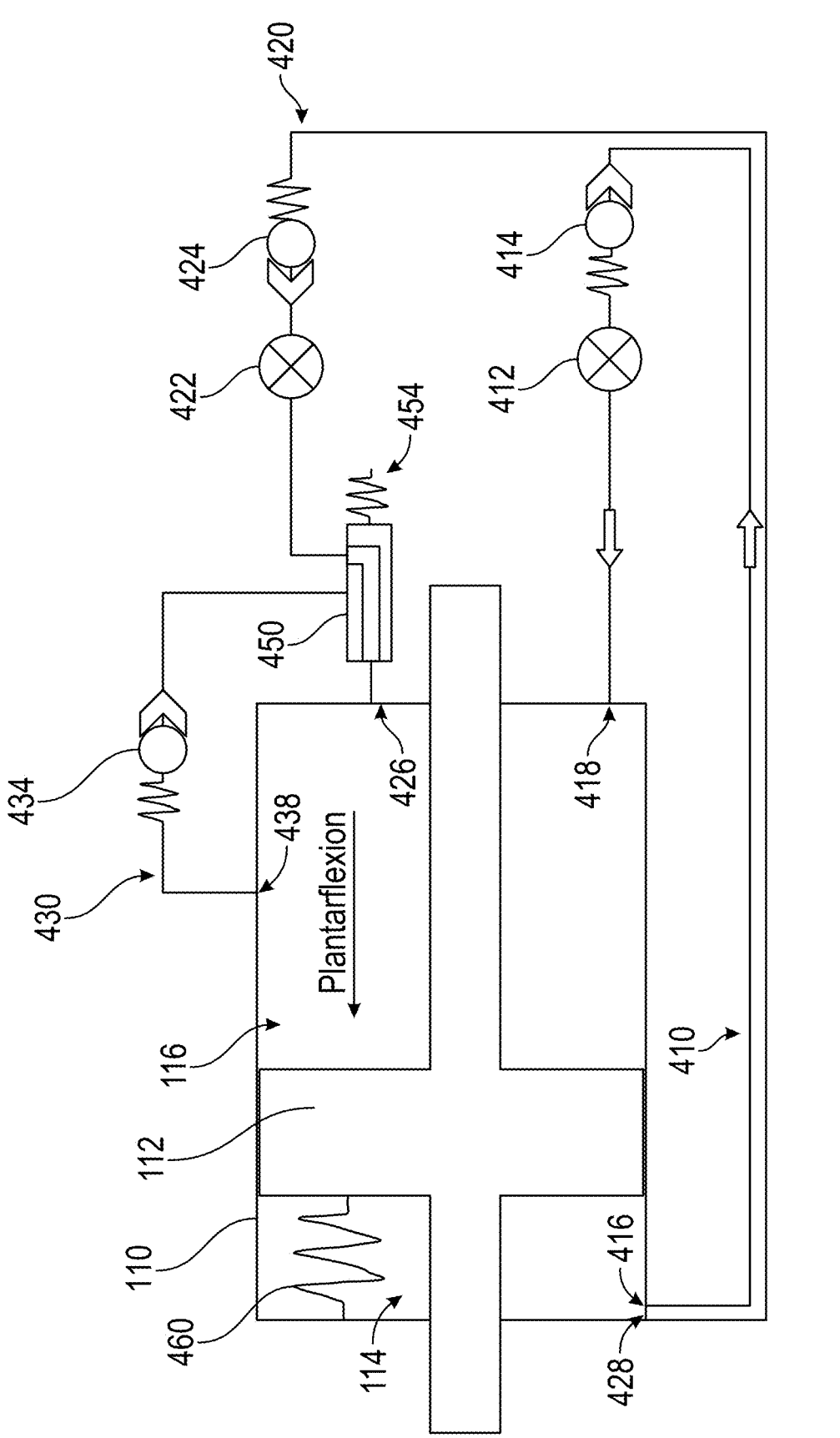
Figure 4C:
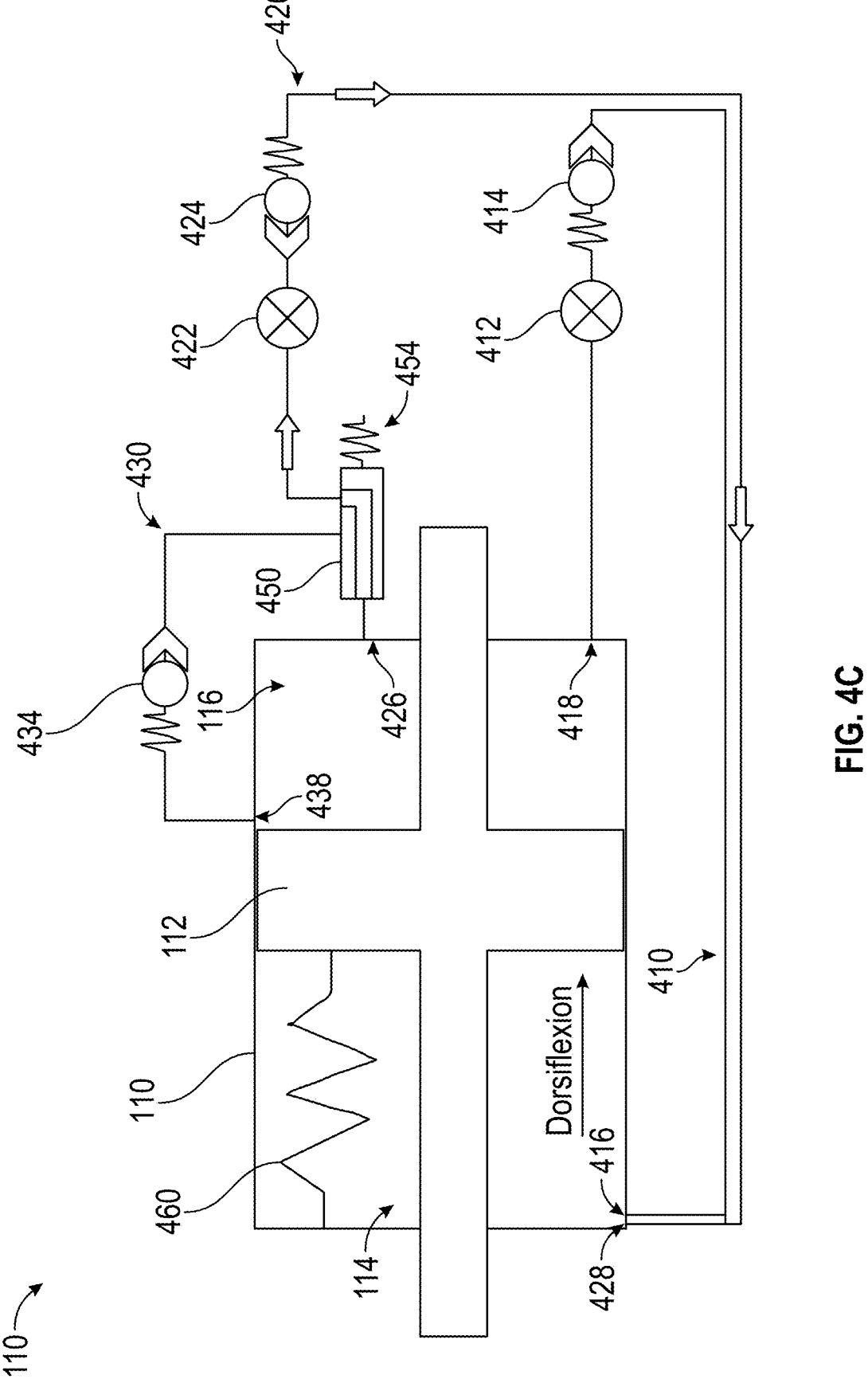

The first check valve 414 can restrict the direction of the flow of hydraulic fluid in the first passage 410. In the example illustrated in FIG. 4A, when the piston 112 moves towards the left end of the schematic illustration of the hydraulic cylinder 110 (e.g., in plantarflexion), the hydraulic fluid in the first chamber 114 can enter into the first passage 410 via the opening 416, flow through the first valve 412 and the first check valve 414, and exit into the second chamber 116 via the opening 418. When the piston 112 moves towards the right end of the schematic illustration of the hydraulic cylinder 110 (for example, as shown in FIG. 4C), e.g. in dorsiflexion, the hydraulic fluid in the second chamber 116 cannot travel from the second chamber 116 to the first chamber 114 via the first passage 410 because the first check valve 414 inhibits (e.g., prevents) flow in that direction.

The second passage can include a second valve 422, a second check valve 424, and openings 426, 428 via which the second passage 420 communicates with the second chamber 116 and first chamber 114, respectively. The second valve 422 is selectively adjustable to adjust a hydraulic damping resistance within the hydraulic system 400. For example, the second valve 422 can restrict the flow of hydraulic fluid through the second passage 420 (e.g., by adjusting a size of an orifice in the valve through which hydraulic fluid flows), which can generate resistance against the movement of the piston 112. In some implementations, the hydraulic dampening resistance generated by the second valve 422 can be varied by adjusting, for example, position, orientation, or configuration of the second valve 422.

The second check valve 424 can restrict the direction of the flow of hydraulic fluid in the second passage 420. In the example illustrated in FIG. 4A, as the piston 112 moves towards the right end of the schematic illustration of the hydraulic cylinder 110 (e.g., in dorsiflexion), the hydraulic fluid in the second chamber 116 can enter into the second passage 420 via the opening 426, flow through the second valve 422 and the second check valve 424, and exit into the first chamber 114 via the opening 428. When the piston 112 moves towards the left end of the schematic illustration of the hydraulic cylinder 110 (e.g. in plantarflexion as shown in FIG. 4B), the hydraulic fluid in the first chamber 114 cannot travel from the first chamber 114 to the second chamber 116 via the second passage 420 because the second check valve 424 inhibits (e.g., prevents) flow in that direction.

The third passage can include a third check valve 434 and an opening 438. The third passage 430 and the second passage 420 can share the opening 426 such that hydraulic fluid can enter through the opening 426 and flow through the second passage 420 or the third passage 430 depending on, for example, the configuration of the diverter valve 450 as described herein.

In the example illustrated in FIG. 4A, the third passage 430 may not include a valve to control (e.g., limit or restrict) the flow of the hydraulic fluid within the third passage 430. As such, the third passage 430 can provide zero, or negligible amount of (e.g., substantially zero), hydraulic dampening resistance when the hydraulic fluid flows through the third passage 430. In the example illustrated in FIG. 4A, the third check valve 434 allows hydraulic fluid to flow from, for example, the opening 426 to the opening 438 via the third passage 430, while inhibiting (e.g., preventing) hydraulic fluid from flowing from the opening 438 to the opening 426 via the third passage 430 because the third check valve 434 inhibits (e.g., prevents) flow in that direction.

The diverter valve 450 can be in (selective) communication with the second passage 420 and the third passage 430. In some implementations, the diverter valve 450 is positioned at a junction between the second passage 420 and the third passage 430.

Figure 4D:
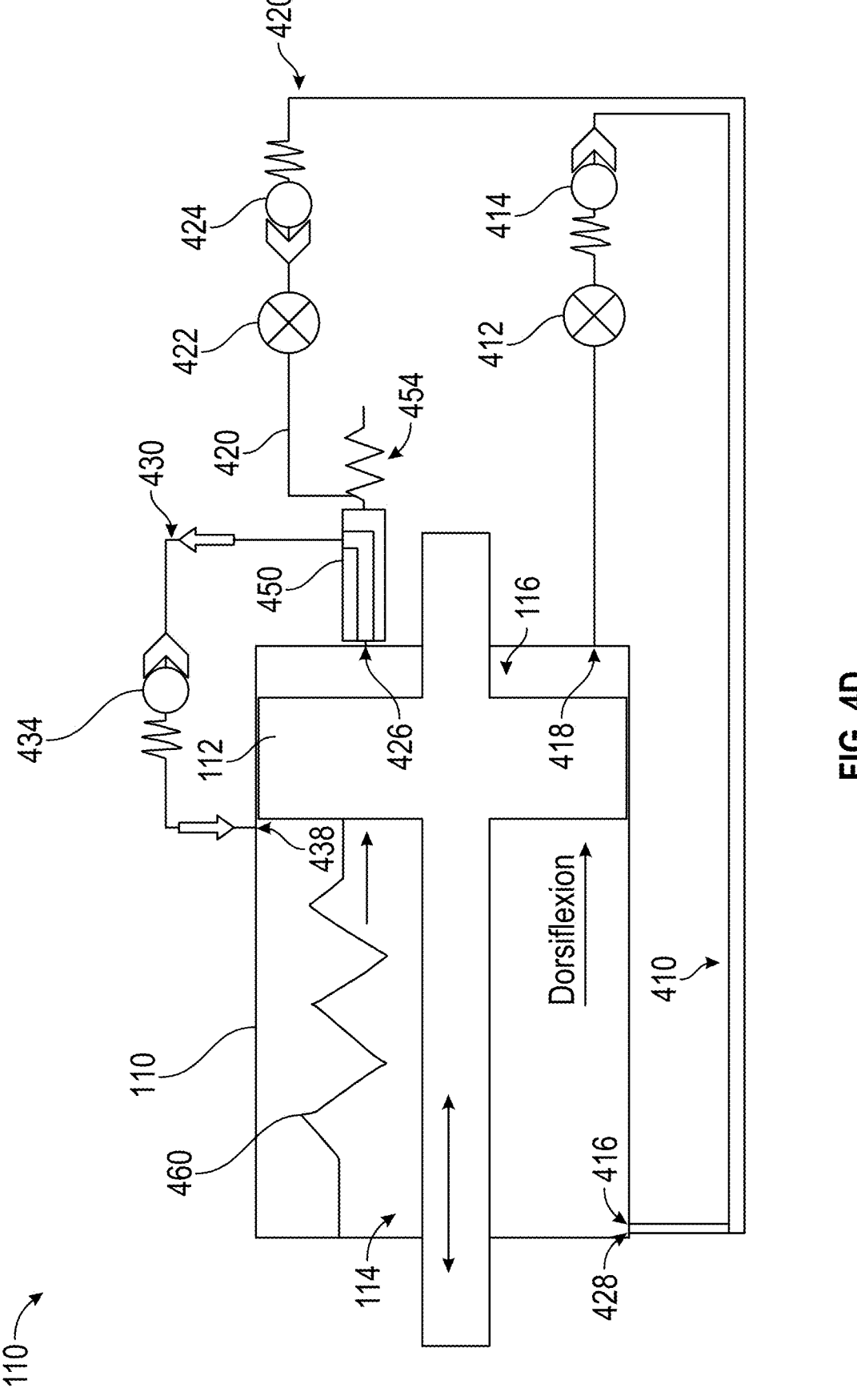

The diverter valve 450 can be coupled to an actuator 454 that can move the diverter valve 450 between different positions (or configurations). For example, the actuator 454 can cause the diverter valve 450 to move in directions 452 as shown in FIG. 4A. The position (or configuration) of the diverter valve 450 can determine whether the hydraulic fluid flows through the second passage 420 or the third passage 430. For example, when the diverter valve 450 is in a first position (for example, as shown in FIG. 4A), the hydraulic fluid can flow from the second chamber 116 to the first chamber 114 via the second passage 420. When the diverter valve 450 is in a second position (for example, as shown in FIG. 4D), the hydraulic fluid can flow from the second chamber 116 to the first chamber 114 via the third passage 430. The actuator 454 can actuate and move the diverter valve 450 between the first position and the second position.

In some implementations, the actuator 454 may be biased to keep the diverter valve 450 in the first position to direct the flow of the hydraulic fluid to the second passage 420 instead of the third passage 430.

With references to FIGS. 4B-4D, operation of the hydraulic system 400 during various stages of the gait cycle is described. Between heel-strike (HS) and mid-stance (MS), the prosthetic device 10 undergoes plantarflexion (that is, the foot portion 20 is moved away from the top portion 102), which changes the angular displacement or position of the bottom portion 104 with respect to the top portion 102 and causes the piston 112 to move upward (for example, away from foot portion 20 in the example illustrated in FIG. 3). The upward movement of the piston 112 during plantarflexion is illustrated as leftward movement of the piston in the schematic illustration shown in FIG. 4B. As the prosthetic device 10 undergoes plantarflexion, the upward movement of the piston 112 causes hydraulic fluid in the hydraulic cylinder 110 to move from the first chamber 114 to the second chamber 116 via the first passage 410 as indicated by the arrows displayed over the first passage 410 in FIG. 4B.

As the hydraulic fluid flows through the first passage 410, the first valve 412 (and/or the first check valve 414) can restrict the flow and generate hydraulic resistance in the hydraulic system 400. The hydraulic resistance generated by the first valve 412 can provide improved gait control for a user of the prosthetic device 10 by, for example, providing smooth transition between heel-strike (HS) and mid-stance (MS).

In some implementations, as the piston 112 moves upward due to the downward movement of the foot portion 20 during plantarflexion (see FIG. 3), an elastic element 460 may be actuated (e.g., compressed). Once actuated, the elastic element 460 can exert a force to the piston 112 and, for example, cause the piston 112 to move rightward as shown in, for example, in FIG. 4C.

The elastic element 460 may be coupled to, for example, the top end of the hydraulic cylinder 110 and a surface of the piston 112 (e.g., a surface facing the top end of the hydraulic cylinder 110) such that downward movement of the foot portion 20 and the hydraulic cylinder 110 during plantarflexion can actuate (e.g., compress) the elastic element 460. In some implementations, the elastic element 460 may be a coil spring wrapped around a shaft of the piston 112 (e.g., a shaft extending between the piston 112 and the top end of the hydraulic cylinder 110) such that movement of the hydraulic cylinder 110 relative to the piston 112 can actuate (e.g., compress) the elastic element 460. In some implementations, the elastic element 460 is operatively coupled to the bottom portion 104 of the prosthetic ankle 100 such that the elastic element 460 applies force to the bottom portion 104 and causes the piston 112 to move.

After mid-stance (MS), the prosthetic device 10 can undergo dorsiflexion until toe-off (TO). During dorsiflexion, the foot portion 20 moves towards the top portion 102, which causes the piston 112 to move downward towards the top plate 12. The downward movement of the piston 112 towards the foot portion 20 can cause the hydraulic fluid in the second chamber 116 to flow to the first chamber 114 as indicated by arrows displayed over the second passage 420. In the example shown in FIG. 4C, the position of the diverter valve 450 causes the hydraulic fluid to flow through the second passage 420 and into the first chamber 114.

As the hydraulic fluid flows through the second passage 420, the second valve 422 (and/or the second check valve 424) can restrict the flow and generate hydraulic resistance in the hydraulic system 400. The hydraulic resistance generated by the second valve 422 can provide better push off for a user of the prosthetic device 10 at toe-off (TO).

As the piston 112 continues to move downward toward the foot portion 20 (or the foot portion 20 continues to move upward towards the top portion 102) during dorsiflexion, the actuator 454 can move the diverter valve 450 to divert the flow of the hydraulic fluid from the second passage 420 to the third passage 430. With reference to examples illustrated in FIGS. 4C and 4D, once the piston 112 is positioned to the right of the opening 438 (or moves past the opening 438) and the pressure amount or the rate of change of pressure sensed by the actuator 454 satisfies certain threshold pressure conditions, the diverter valve 450 can divert the flow of hydraulic fluid, for example, from the second passage 420 (for example, a restricted flow passage) to the third passage 430 (for example, a non-restricted flow passage).

The threshold pressure conditions may be associated with the amount of or the rate of change of hydraulic pressure and a threshold value. For example, the threshold pressure conditions may be satisfied if the amount of hydraulic pressure (or the rate of change of the hydraulic pressure) is greater than, greater than equal to, equal to, less than, or less than equal to the threshold value. The threshold value may be a pressure value or a rate of change of pressure.

In some implementations, the amount of or the rate of change of pressure may be associated with the hydraulic system 400. In some implementations, the amount of or the rate of change of pressure may be measured or sensed in the second chamber 116. In some implementations, the actuator 454 may sense the amount of or the rate of change of pressure (for example, at the actuator 454) during dorsiflexion.

As the piston 112 moves downward during dorsiflexion (see FIG. 4C), the hydraulic pressure within the second chamber 116 and around the opening 426 can increase during the earlier portion of the dorsiflexion (e.g., following transition from plantarflexion to dorsiflexion). The increase of the hydraulic pressure can be caused by the hydraulic dampening resistance of the second passage 420 and the downward movement (or rightward movement in the schematic illustration shown in FIG. 4C) of the piston 112 corresponding to the forward rotation of the ankle 100 relative to the foot 20. However, as the piston 112 continues to move downward during dorsiflexion (see FIG. 4D), the movement of the piston 112 can slow down (e.g., as the rotation of the ankle 100 relative to the foot 20 slows down when approaching the end of dorsiflexion and toe off), which can cause the hydraulic pressure to decrease. Additionally, the slowing down of the piston 112 during dorsiflexion can decrease the rate of change of the hydraulic pressure. Such decrease in the hydraulic pressure or in the rate of change of the hydraulic pressure during dorsiflexion can be used to determine when to change the position of the diverter valve 450 and trigger non-resistance flow of the hydraulic fluid between the second chamber 116 and the first chamber 114.

In some implementations, the actuator 454 can detect the hydraulic pressure within the second chamber 116. For example, the actuator 454 can be a pressure activated (e.g., spring loaded) actuator that actuates at a particular pressure threshold or rate or pressure threshold. In one implementation, when the hydraulic pressure drops below a threshold value (e.g., a threshold pressure value) during dorsiflexion, the actuator 454 can cause the diverter valve 450 to move and divert the flow of the hydraulic fluid from the second passage 420 to the third passage 430. The threshold value (e.g., a threshold pressure value) can be predetermined (e.g., by a manufacturer). In some implementations, the threshold value can be adjusted by the user by, for example, adjusting configuration (e.g., sensitivity) of the actuator 454.

In some implementations, the actuator 454 can detect the rate of change of the hydraulic pressure within the second chamber 116. When the rate of change of the hydraulic pressure drops below a threshold value (e.g., a threshold rate of change of pressure) during dorsiflexion, the actuator 454 can cause the diverter valve 450 to move and divert the flow of the hydraulic fluid from the second passage 420 to the third passage 430. The threshold value (e.g., a threshold rate of change of pressure) can be predetermined (e.g., by a manufacturer). In some implementations, the threshold value can be adjusted by the user by, for example, changing configuration (e.g., sensitivity) of the actuator 454.

Once the flow is diverted to the third passage 430, because the third passage 430 provides no or negligible hydraulic resistance, the hydraulic fluid of the hydraulic system 400 can easily flow from the second chamber 116 to the first chamber 114 (without resistance) via the third passage 430. The non-restricted (that is, with no or negligible hydraulic resistance) flow of the hydraulic fluid from the second chamber 116 to the first chamber 114 can eliminate or reduce the hydraulic resistance generated by the hydraulic system 400 and allow the piston 112 to move towards the maximum-dorsiflexion position (that is, the rightmost end of the hydraulic cylinder 110 shown in FIG. 4A) with more ease due to the force exerted by the elastic element 460 (e.g., spring) on the piston 112. In some implementations, the restoring force exerted by the elastic element 460 can further aid the movement of the piston 112 towards the maximum-dorsiflexion position (e.g. toe-up position) during the swing phase.

In some implementations, the position of the opening 438 can correspond to the position of the foot portion 20 (or the bottom portion 104) with respect to the top portion 102 at toe-off (TO). For example, the opening 438 can be positioned such that the piston 112 moves past the opening 438 at the same time when toe-off (TO) occurs (or when the swing phase begins).

After toe-off (TO), the gait cycle enters the swing phase. When the swing phase begins, the prosthetic device 10 is off the ground and experiences zero or negligible (e.g., substantially zero) amount of external force that, for example, causes the foot portion 20 to pivot with respect to the top portion 102 about the axle 106. As such, there is no movement of the piston 112 caused by the external force in the beginning of the swing phase after toe-off (TO) and the hydraulic pressure reaches zero or become negligible (e.g., substantially zero). Once the hydraulic pressure reaches zero or negligible, the elastic element 460 can push the piston 112 towards the maximum-dorsiflexion position (or maximum toe-up position) by exerting force (directly or indirectly) against the piston 112 towards the direction associated with dorsiflexion.

The actuator 454 can, after the swing phase, move the diverter valve 450 so that the hydraulic fluid is no longer diverted to the third passage 430. In some implementations, the movement of the diverter valve 450 to shift the flow from the third passage 430 to the second passage 420 can occur when the piston 112 begins to move in the plantarflexion direction (as shown in FIGS. 4A and 4B) at heel-strike (HS). At heel-strike (HS) the prosthetic device 10 undergoes plantarflexion again, which causes the hydraulic fluid to move from the first chamber 114 to the second chamber 116 via the first passage 410 as described herein. Alternatively, in some implementations, the dorsiflexion movement of the piston 112 (e.g., as shown in FIG. 4C) after heel-strike (HS) can increase hydraulic pressure within the second chamber 116 (e.g., hydraulic pressure sensed by the actuator 454), and this change in hydraulic pressure (e.g., pressure increase sensed by the actuator 454) can cause the actuator 454 to move the diverter valve 450 to shift the flow from the third passage 430 to the second passage 420. For example, the diverter valve 450 may shift from the third passage 430 to the second passage 420 when the pressure in the second chamber 116 (e.g., pressure detected by the actuator 454) is above a threshold value (e.g., a threshold pressure value).

Figure 6:
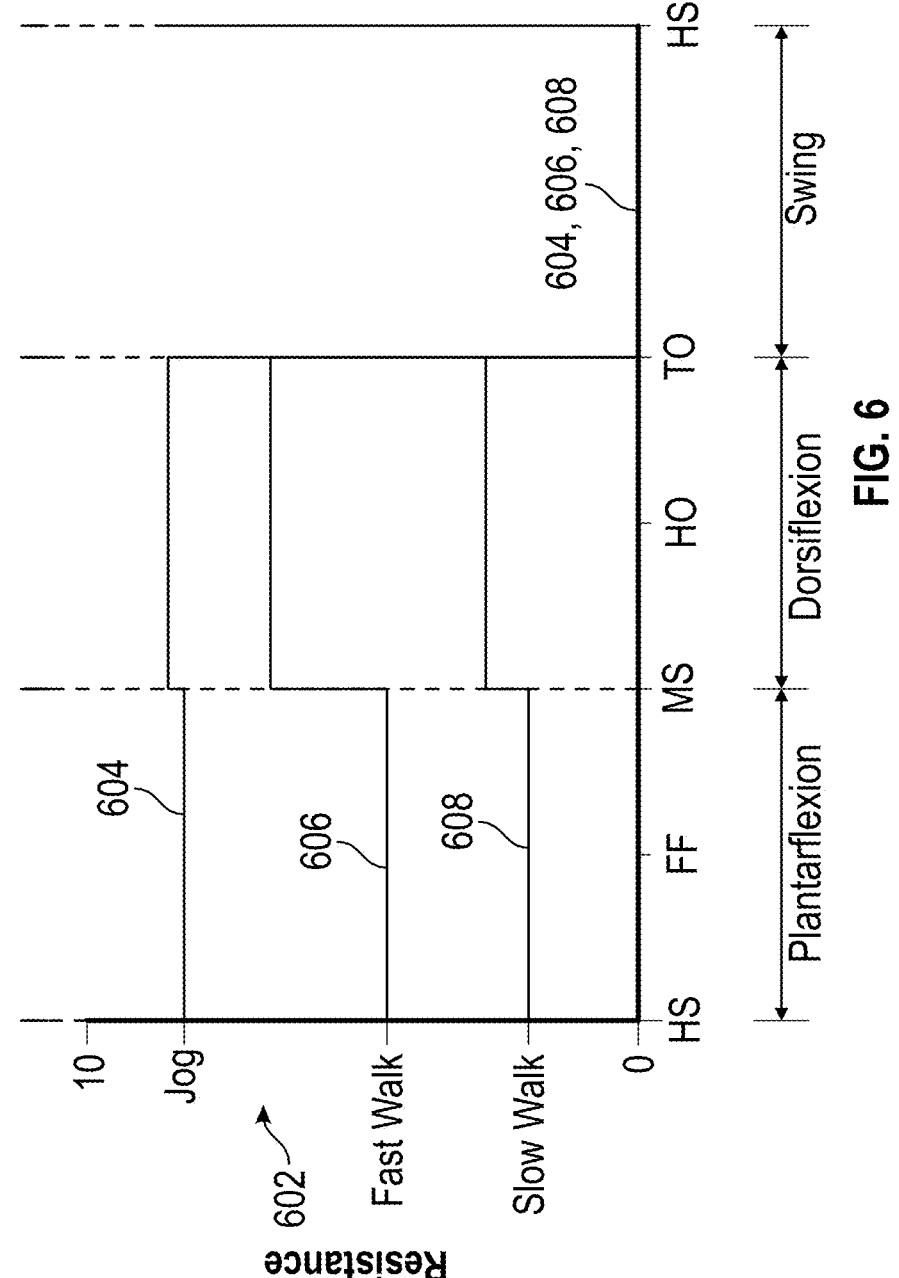
FIG. 6 schematically shows a graph of hydraulic resistance of an embodiment of a hydraulic prosthetic ankle during different phases of gait for different modes of operation.

In some implementations, the default configuration of the diverter valve 450 is to divert the flow to the third passage 430 unless stance phase dorsiflexion movement occurs (e.g., the prosthetic device 10 is undergoing dorsiflexion between mid-stance (MS) and toe-off (TO) as shown in FIG. 6). For example, the diverter valve 450 diverts flow of hydraulic fluid to the second passage 420 during the stance phase dorsiflexion and diverts flow of hydraulic fluid to the third passage 430 during the swing phase and the stance phase plantarflexion.

Figure 5:
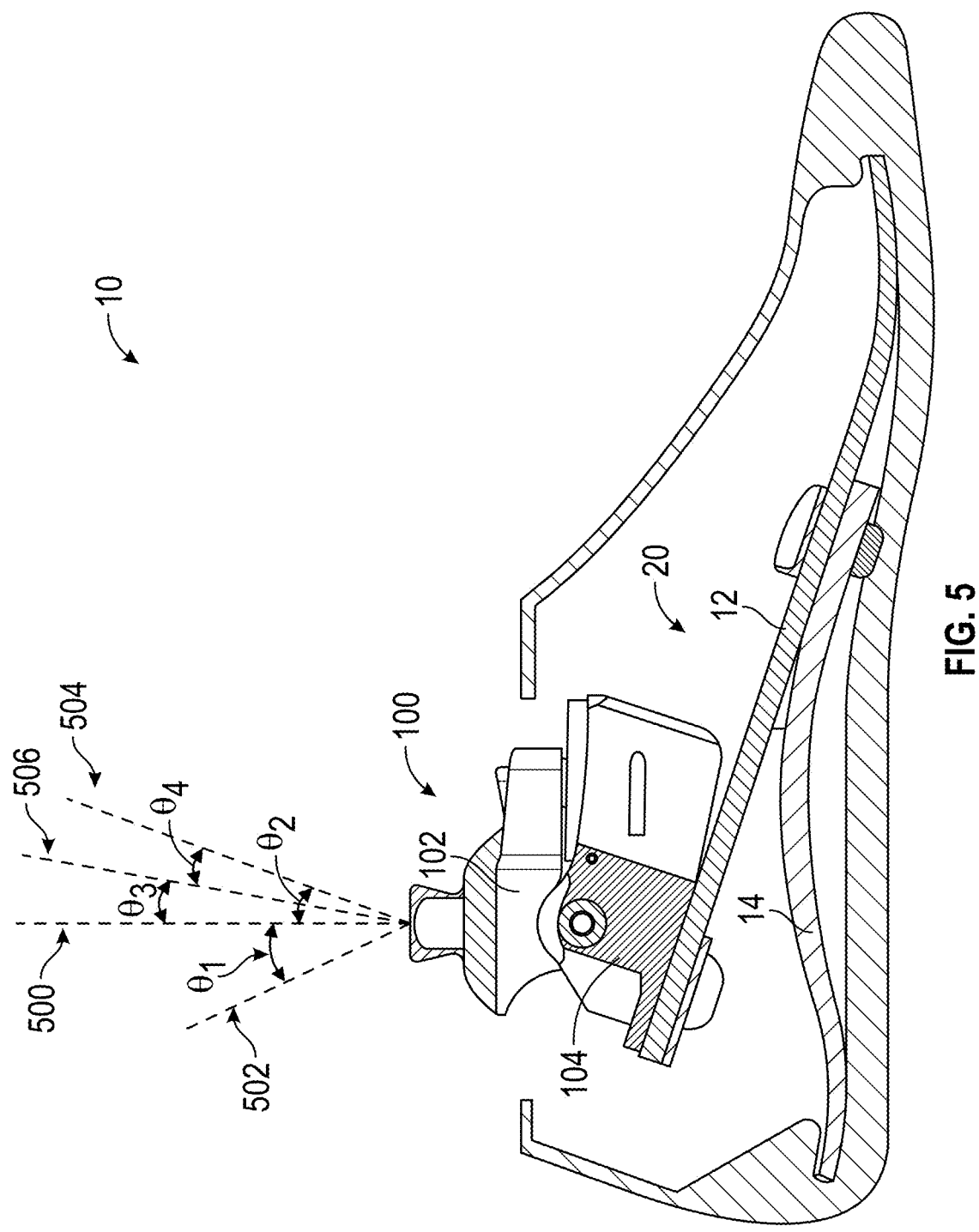
FIG. 5 illustrates different angular positions of the hydraulic prosthetic ankle during different phases of gait.

FIG. 5 illustrates various angular positions of the top portion 102 with respect to the bottom portion 104 (or the foot portion 20) during the gait cycle. The angular positions, which represented by lines 500, 502, 504, 508, can be relative angular positions between the top portion 102 and the bottom portion 104. The line 500 represents the neutral position at which the foot portion 20 is in neither plantarflexion nor dorsiflexion. The line 502 represents the maximum plantarflexion position, which the line 504 represents the maximum dorsiflexion position. The angle θ1 represents the maximum angular displacement for the prosthetic device 10 during plantarflexion and the angle θ2 represents the maximum angular displacement for the prosthetic device 10 during dorsiflexion.

The line 506 can represent the relative angular displacement between the top portion 102 and, for example, the foot portion 20 when, for example, the swing phase of the gait cycle begins. In some implementations, the line 506 can represent the relative angular displacement between the top portion 102 and the foot portion 20 at the toe-off (TO). In some implementations, the line 506 represents the relative angular displacement between the top portion 102 and, for example, the foot portion 20 at which the piston 112 moves past the opening 438 during dorsiflexion as described herein. In some implementations, the line 506 represents the angular position of the foot portion 20 at which the diverter valve 450 moves to divert the flow of the hydraulic fluid from the second passage 420 to the third passage 430 to allow non-resistance flow of the hydraulic fluid from the second chamber 116 to the first chamber 114.

Once the relative angular displacement between the top portion 102 and the foot portion 20 reaches θ3 during dorsiflexion and a pressure sensed at the actuator 454 (e.g., sensed by the actuator 454) satisfies a pressure threshold condition, the diverter valve 450 can move to a diverting position (e.g., the second position as described herein) to divert the flow of hydraulic fluid from the second passage 420 to the third passage 430 and begin the non-resistance flow of the hydraulic fluid through the third passage 430. The pressure threshold condition may include the pressure inside the second chamber 116 being less than a predetermined pressure threshold value. As described herein, the non-resistance flow of the hydraulic fluid through the third passage 430 can facilitate the foot portion 20 to move towards the maximum dorsiflexion position (that is, the relative angular displacement associated with the line 504 between the top portion 102 and the foot portion 12). In some implementations, the diverter valve 450 can move to the diverting position when the angular displacement between the top portion 102 and the foot portion 20 reaches $\theta_3$ during dorsiflexion regardless of the pressure in the second chamber 116. The angle $\theta_4$ represents the additional angular displacement of the foot portion 20 facilitated by the non-resistance flow of the hydraulic fluid as described herein. The additional angular displacement can further be facilitated by the restoring force exerted by the elastic element 460 again the piston 112.

FIG. 6 illustrates a graph showing example hydraulic resistance 602 generated by the hydraulic system 400 of the prosthetic ankle 100 during different stages of gait. The hydraulic resistance levels 604, 606, 608 illustrate the relative amount of hydraulic resistance experienced by the hydraulic system 400 during slow walk, fast walk, and jogging, respectively. As shown in the graph illustrated in FIG. 6, the amount of hydraulic resistance experienced by the hydraulic system 400 of the prosthetic ankle 100 can in one example increase when the prosthetic device 10 begins to undergo dorsiflexion after mid-stance (MS). After toe-off (TO), the prosthetic device 10 can enter into the swing phase of gait and can experience reduced or zero hydraulic resistance. As described herein, the diverter valve 450 of the hydraulic system 400 can divert the flow of hydraulic fluid within the hydraulic system 400 to reduce the hydraulic resistance experienced by the hydraulic system 400 (for example, the piston 112). The reduced or zero hydraulic resistance can facilitate, for example, the foot portion 20 of the prosthetic device 10 to reach the maximum-dorsiflexion position as described herein, and thereby reduce the likelihood of accidental contact between the prosthetic device 10 and the ground during the swing phase.

In some implementations, the hydraulic dampening resistance generated by the hydraulic system 400 varies because of the first valve 412 and the second valve 422. For example, the first valve 412 and the second valve 422 can be adjusted to generate different amounts of hydraulic dampening resistance when the hydraulic fluid flows through the first passage 410 and the second passage 420, respectively. For example, the hydraulic dampening resistance generated by the first valve 412 during plantarflexion (that is, between heel-strike (HS) and mid-stance (MS) shown in FIG. 6) can be less than that of the second valve 422 during dorsiflexion (that is, between mid-stance (MS) and toe-off (TO)). The relatively-less hydraulic dampening resistance generated by the first valve 412 can allow a user of the prosthetic device 10 to have a smooth transition between heel-strike (HS) and mid-stance (MS), while the relatively greater hydraulic dampening resistance generated by the second valve 422 can allow the user to push off the ground with greater amount of force.

Figure 7:
FIG. 7 illustrates a flowchart for a method of operating a diverter to a hydraulic system.

FIG. 7 illustrates a flowchart for a process 700 of operating a diverter valve 450 that may be executed by the hydraulic system 400. The steps of the process are indicated by blocks 702 to 712. The process 700 starts at block 702. At block 704, a determination is made whether a first condition is satisfied. If the first condition is not satisfied, the method 700 proceeds to block 702. If the first condition is satisfied, the process 700 proceeds to block 706. As described herein, the first condition can include the piston 112 moving past the opening 438 during dorsiflexion and a pressure amount or a rate of change of pressure sensed by the actuator 454 satisfies a first threshold pressure condition. In some implementations, the pressure amount or the rate of change of pressure may be less than equal to a threshold value to satisfy the first threshold pressure condition.

At block 706, the position of the diverter valve 450 is changed from a first position to a second position. As described herein, when the diverter valve 450 is in the first position, the hydraulic fluid in the hydraulic system 400 can flow from the second chamber 116 to the first chamber 114 via the second passage 420. Once the diverter valve 450 is in the second position, the hydraulic fluid in the hydraulic system 400 can flow from the second chamber 116 to the first chamber 114 via the third passage 430.

At block 708, the process 700 waits. At block 710, a determination is made whether a second condition is satisfied. If the second condition is not satisfied, the process 700 proceeds to block 708. If the second condition is satisfied, the process 700 proceed to block 712, where the position of the diverter valve 450 is changed from the second position to the first position. The second condition can include the piston 112 moving past the opening 438 during plantarflexion and a pressure amount or a rate of change of pressure sensed by the actuator 454 satisfying a second threshold pressure condition. In some implementation, the pressure amount or the rate of change of pressure may be greater than or equal to (or less than or equal to) a threshold value to satisfy the second threshold pressure condition. The pressure threshold conditions associated with the first condition and the second condition (that is, the first threshold pressure condition and the second threshold pressure condition) may be different or the same. After the position of the diverter valve 450 is changed from the second position to the first position, the process 700 proceeds to block 702.

FIGS. 8-15 show a schematic view or schematic illustration of a prosthetic device 10A. Some of the features of the prosthetic device 10A are similar to features of the prosthetic device 10 in FIGS. 1-7. Thus, reference numerals used to designate the various features or components of the prosthetic device 10A are identical to those used for identifying the corresponding features or components of the prosthetic device 10 in FIGS. 1-7, except that an "A" has been added to the numerical identifier. Therefore, the structure and description for the various features of the prosthetic device 10 and how it's operated in FIGS. 1-7 are understood to also apply to the corresponding features of the prosthetic device 10A in FIGS. 8-10, except as described below.

Figure 8:
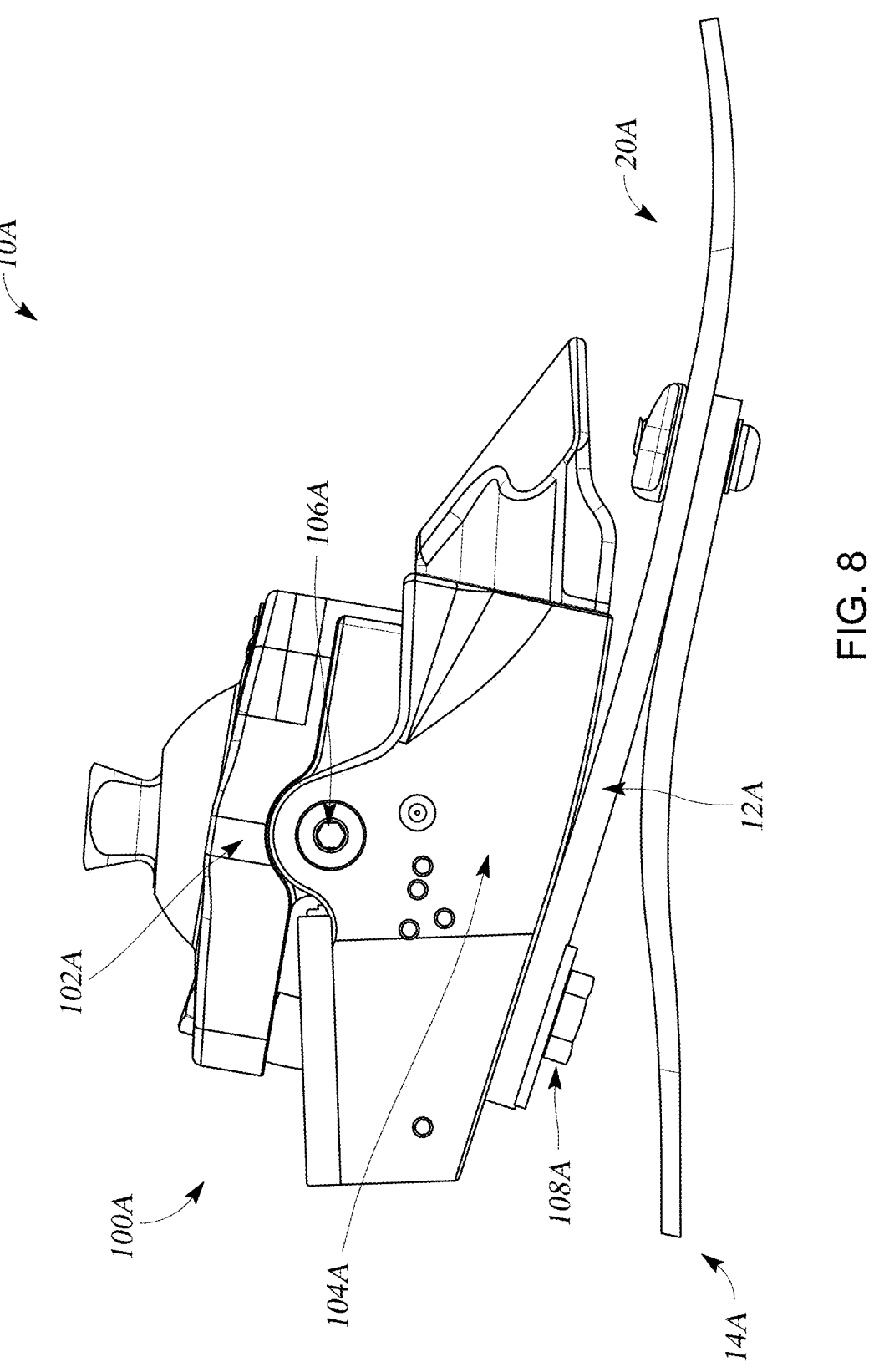
FIG. 8 shows a schematic side view of an embodiment of a prosthetic or orthotic device with a hydraulic prosthetic ankle.
Figure 9:
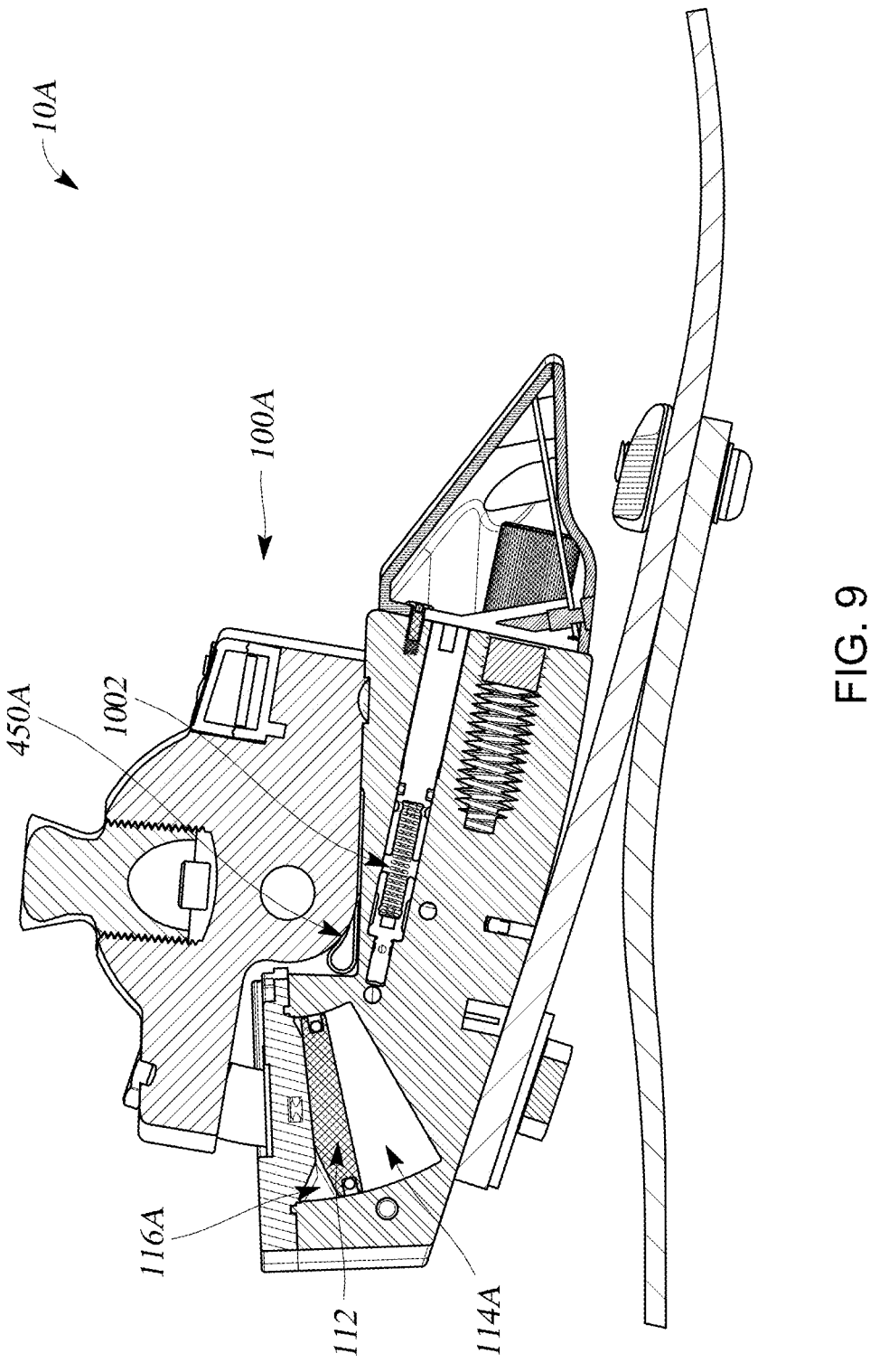
FIG. 9 illustrates a schematic partial cross-sectional view of an embodiment of a prosthetic or an orthotic device with a hydraulic prosthetic ankle.

FIG. 8 shows a perspective view of a prosthetic device 10A (e.g., a prosthetic foot) which can include a hydraulic prosthetic ankle 100A and a foot portion 20A. The foot portion 20A can include a top plate 12A, and a heel plate 14A. The hydraulic prosthetic ankle 100A can include a top portion 102A and a bottom portion 104A that are rotatably coupled via an axle 106A. The bottom portion 104A can be coupled to the top plate 12A of the foot portion 20A using, for example, one or more fasteners (e.g., bolts, screws) 108A such that movement of, for example, the bottom portion 104A translates to foot portion 20A. For example, angular displacement of the bottom portion 104A with respect to the top portion 102A (e.g., plantarflexion or moving downward and away from the top portion 102A) can cause the foot portion 20A to undergo angular displacement with respect to the top portion 102A. Other suitable devices or connectors may be used to couple the bottom portion 104A of the hydraulic prosthetic ankle 100A with the top plate 12A. The top plate 12A can be coupled to a heel plate 14A with one or more fasteners (e.g., bolts, screws). The heel plate 14A can extend rearward to a free end. In some implementations, the heel plate 14A can include an arch as shown in FIGS. 8-9. The top portion 102A can be used to couple the prosthetic device 10A to a user's residual limb (e.g., a calf) via, for example, a pylon and socket. The prosthetic ankle 100A may further include a drain passageway 1002 as shown in FIGS. 9-10.

Figure 10:
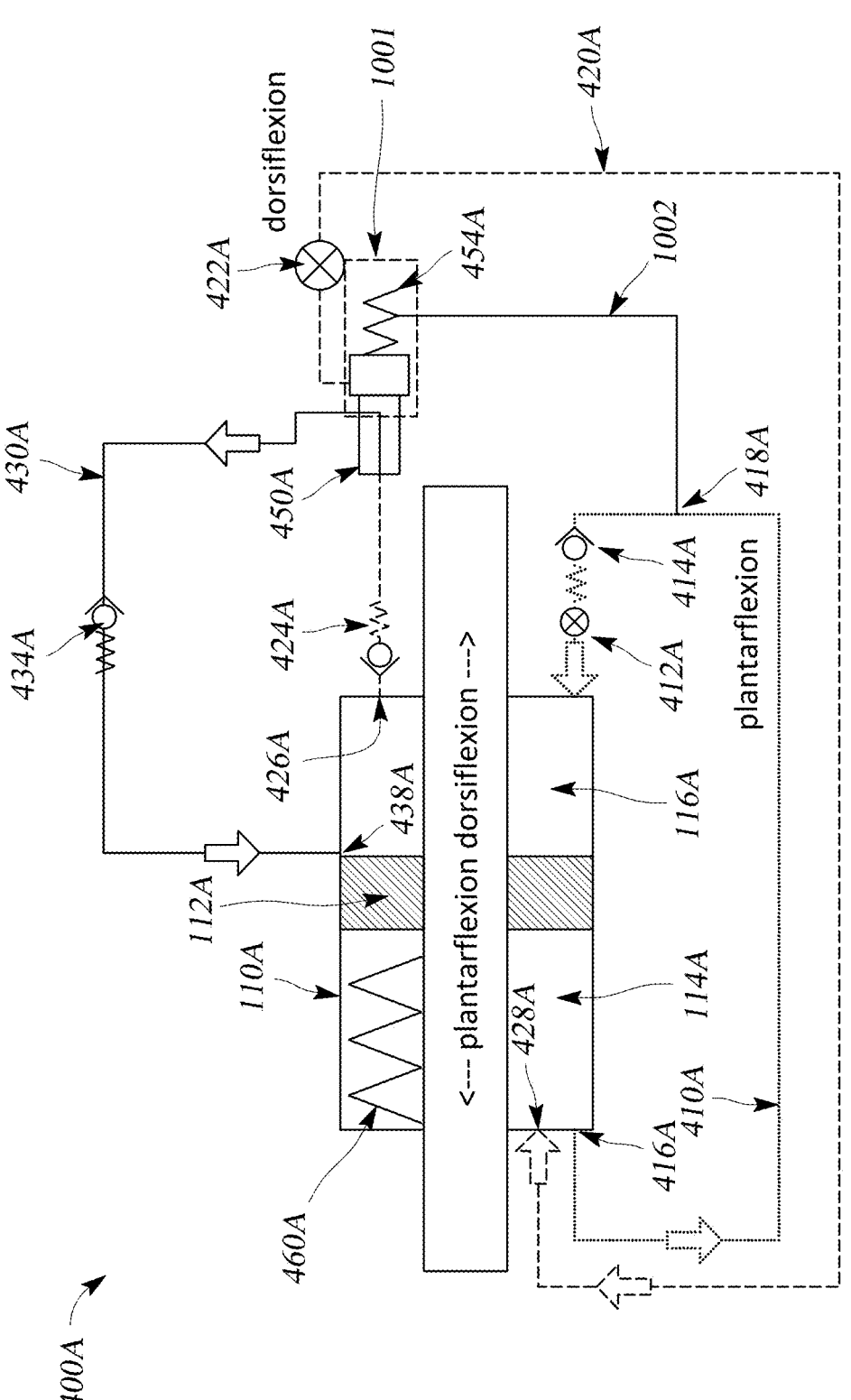
FIG. 10 schematically illustrates operation of an embodiment of a hydraulic prosthetic ankle during different phases of gait.

FIG. 10 schematically illustrates a hydraulic system 400A of the hydraulic prosthetic ankle 100A. In the example illustrated in FIG. 10, the hydraulic system 400A can include the hydraulic cylinder 110A, the piston 112A, the first chamber 114A, and the second chamber 116A as described herein. In addition, the hydraulic system 400A can include a first passage 410A, a second passage 420A, a third passage 430A, and a diverter valve 450A. The hydraulic system 400A may further include a drain passageway 1002 connecting a chamber 1001 housing the diverter valve 450A and the actuator 454A to the first passage 410A. In some implementations, the drain passageway 1002 may connect the chamber 1001 housing the diverter valve 450A and the actuator 454A to one or both of the first chamber 114A or the second chamber 116A. The components of the hydraulic system 400A can control the flow of hydraulic fluid within the hydraulic system 400A to provide improved control of the relative angular positions or movements of the top portion 102A and the bottom portion 104A of the prosthetic device 10A during gait.

The piston 112A may be coupled to an elastic element 460A (e.g., a coil spring) on one end in such a way as to bias the hydraulic system 400A in the dorsiflexion direction. During a dorsiflexion motion of the prosthetic device 10A (e.g., movement of the piston 112A toward the right in FIG. 10), when high pressure (e.g., pressure above a threshold amount, or rate of change of pressure above a certain threshold) is applied to the diverter valve 450A (e.g., as sensed by the actuator 454A), the diverter valve 450A will shift towards the right side of the schematic illustration, connecting a pathway which would allow fluid to flow from the second chamber 116A of the cylinder 110A along the second passage 420A via the second check valve 424A, then the diverter valve 450A, and then the second valve 422A before connecting to the first chamber 114A of the cylinder 110A. As the diverter valve 450A is shifted towards the right, the chamber 1001 housing the diverter valve 450A and the actuator 454A reduces in volume, and therefore compresses the actuator 454A. When the actuator 454A is compressed, hydraulic oil is expelled from the chamber 1001 and allowed to flow through drain passageway 1002. The drain passageway allows the volume of the chamber in which the actuator 454A is disposed and that is behind (e.g., to the right of) the diverter valve 450A to be pressure balanced so that the diverter valve 450A can move freely based on the specified thresholds of the hydraulic system 400A.

During a dorsiflexion motion of the prosthetic device 10A (e.g., movement of the piston 112A toward the right in FIG. 10), when low pressure (e.g., pressure below a threshold amount, or rate of change of pressure below a certain threshold) is applied to the diverter valve 450A (e.g., as sensed by the actuator 454A) and the piston 112A is located to the right of the opening 438A, the diverter valve 450A would be shifted towards the left side of the schematic illustration, connecting a pathway which would allow fluid to flow from the second chamber 116A of the cylinder 110A along the third passage 430A via the second check valve 424A, then the diverter valve 450A and then the third check valve 434A to the opening 438A to pass into the first chamber 114.

In operation, as the piston 112A moves during dorsiflexion of the prosthetic device 10A, the hydraulic pressure within the second chamber 116A and around the opening 426A can increase during the earlier portion of the dorsiflexion (e.g., following transition from plantarflexion to dorsiflexion). The increase of the hydraulic pressure can be caused by the hydraulic dampening resistance of the second passage 420A and the downward movement (or rightward movement in the schematic illustration shown in FIG. 10) of the piston 112A corresponding to the forward rotation of the prosthetic ankle 100 relative to the foot portion 20A. However, as the piston 112A continues to move downward during dorsiflexion, the movement of the piston 112A can slow down (e.g., as the rotation of the ankle 100A relative to the foot 20A slows down when approaching the end of dorsiflexion and toe off), which can cause the hydraulic pressure to decrease. Additionally, the slowing down of the piston 112A during dorsiflexion can decrease the rate of change of the hydraulic pressure. Such decrease in the hydraulic pressure or in the rate of change of the hydraulic pressure during dorsiflexion can be used to determine when to change the position of the diverter valve 450A and trigger non-resistance flow (e.g., flow along third passage 430A of the hydraulic fluid between the second chamber 116A and the first chamber 114A.

As discussed above in connection with FIG. 6, once the flow is diverted to the third passage 430A, because the third passage 430A provides no or negligible hydraulic resistance, the hydraulic fluid of the hydraulic system 400A can easily flow from the second chamber 116A to the first chamber 114A (without resistance) via the third passage 430A. The non-restricted (that is, with no or negligible hydraulic resistance) flow of the hydraulic fluid from the second chamber 116A to the first chamber 114A can eliminate or reduce the hydraulic resistance generated by the hydraulic system 400A and allow the piston 112A to move towards the maximum-dorsiflexion position (that is, the rightmost end of the hydraulic cylinder 110A shown in FIG. 10) with more ease due to the force exerted by the elastic element 460A (e.g., spring, coil spring) on the piston 112A. In some implementations, the restoring force exerted by the elastic element 460A can further aid the movement of the piston 112A towards the maximum-dorsiflexion position (e.g. toe-up position) during the swing phase.

Figure 11:
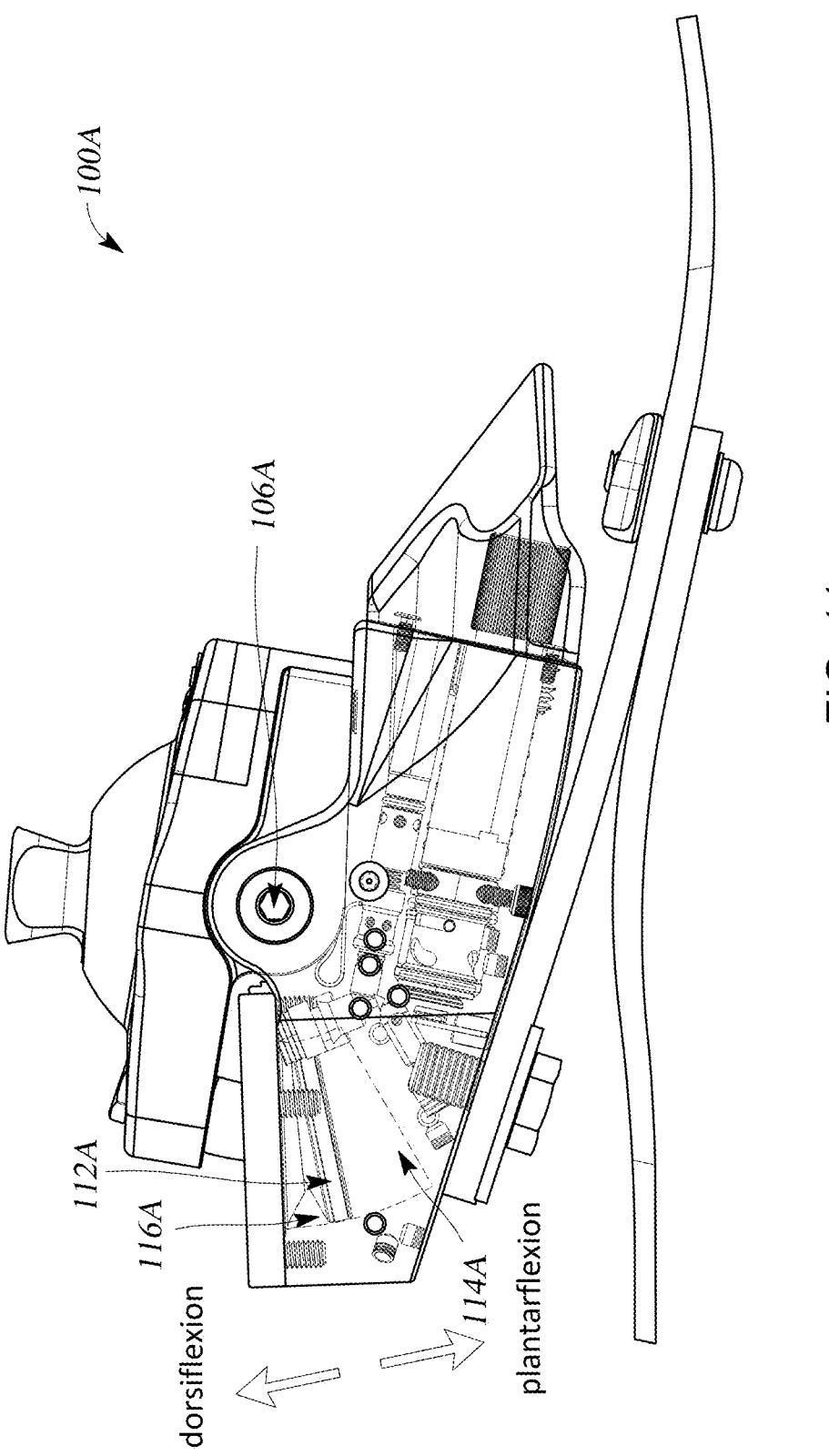
FIG. 11 illustrates a schematic side view of an embodiment of a prosthetic or an orthotic device with a hydraulic prosthetic ankle, showing the ankle housing as transparent to show components inside the ankle housing.

FIG. 11 illustrates a schematic partial cross-sectional of the prosthetic ankle 100A. Plantarflexion motion of the prosthetic device 10A will cause the piston 112A to move up within the cylinder and cause the first chamber 114A of the prosthetic ankle 100A to get smaller as the prosthetic ankle 100A rotates clockwise relative to axle 106A. Conversely, dorsiflexion will cause the piston 112A to move down within the cylinder and cause the second chamber 116A of the prosthetic ankle 100A to get smaller as the prosthetic ankle 100A rotates counter-clockwise relative to axle 106A.

Figure 12:
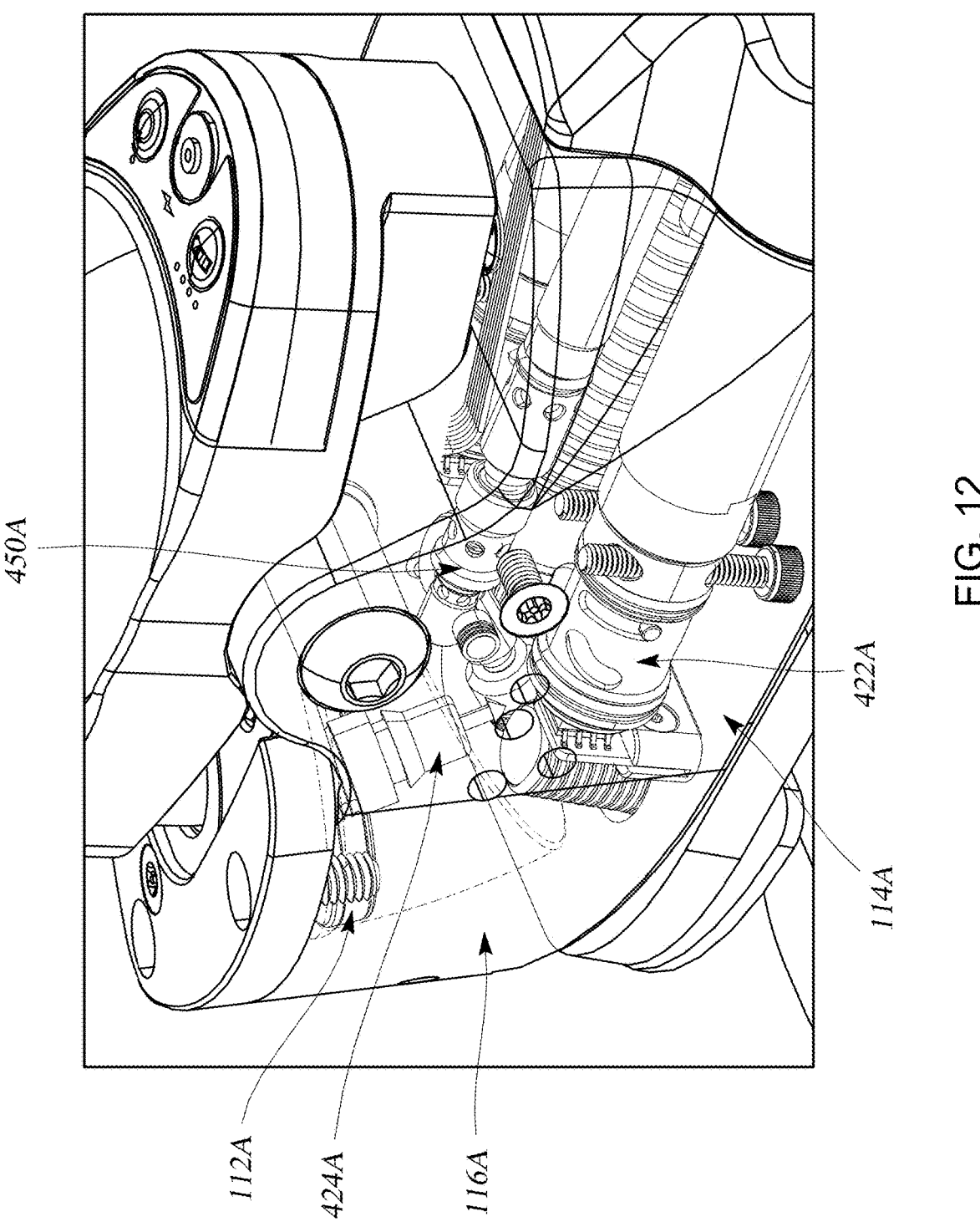
FIG. 12 shows a perspective view of a portion of a hydraulic system for the hydraulic prosthetic ankle in FIG. 11.
Figure 13:
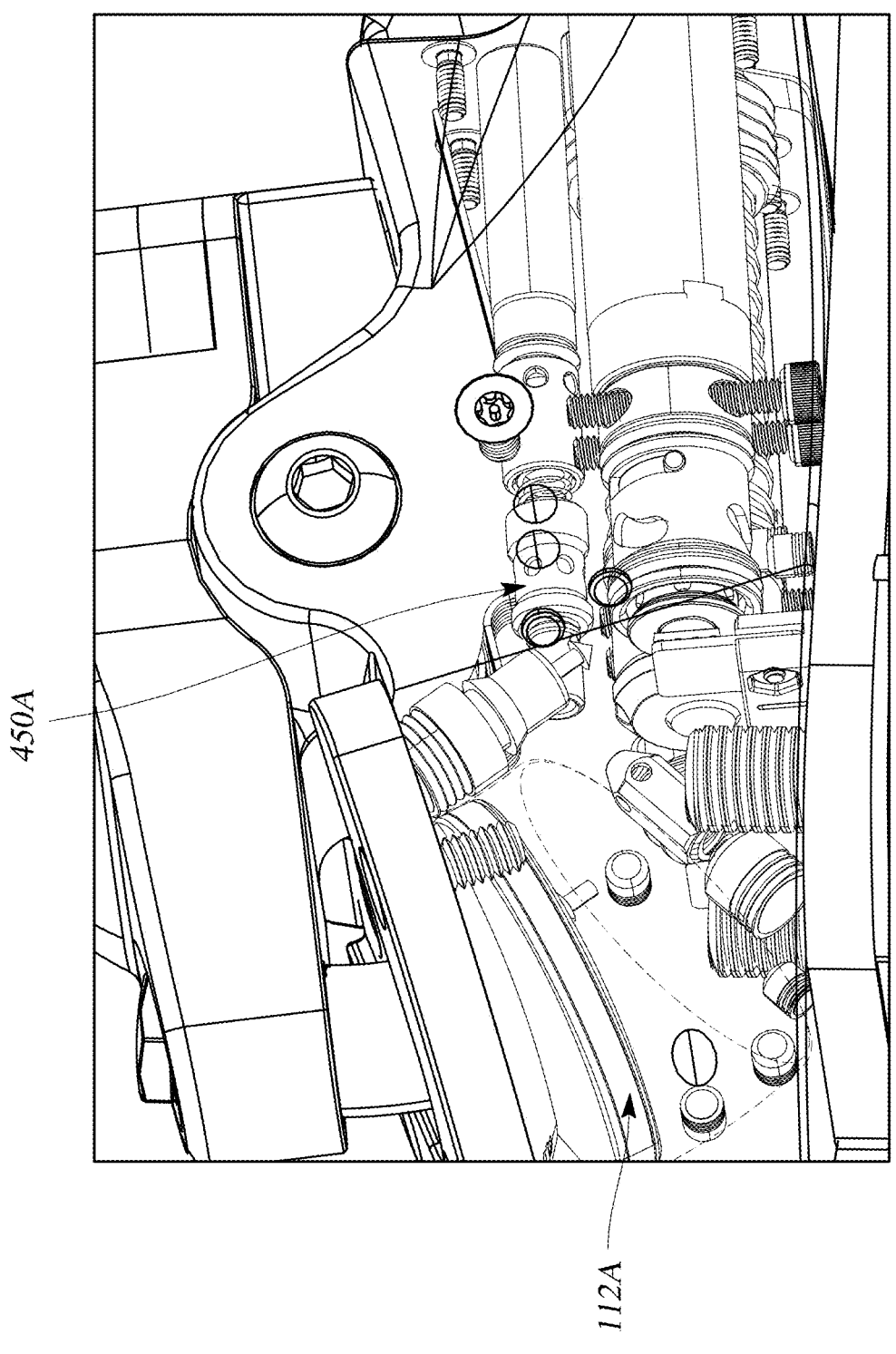
FIG. 13 shows a perspective view of a portion of a hydraulic system for the hydraulic prosthetic ankle in FIG. 11.

FIGS. 12-13 show the arrangement of components of the hydraulic system 400A within the prosthetic ankle 100A, in particular one implementation of the arrangement of the diverter valve 450A and second check valve 424A and the second valve 422A.

Figure 14:
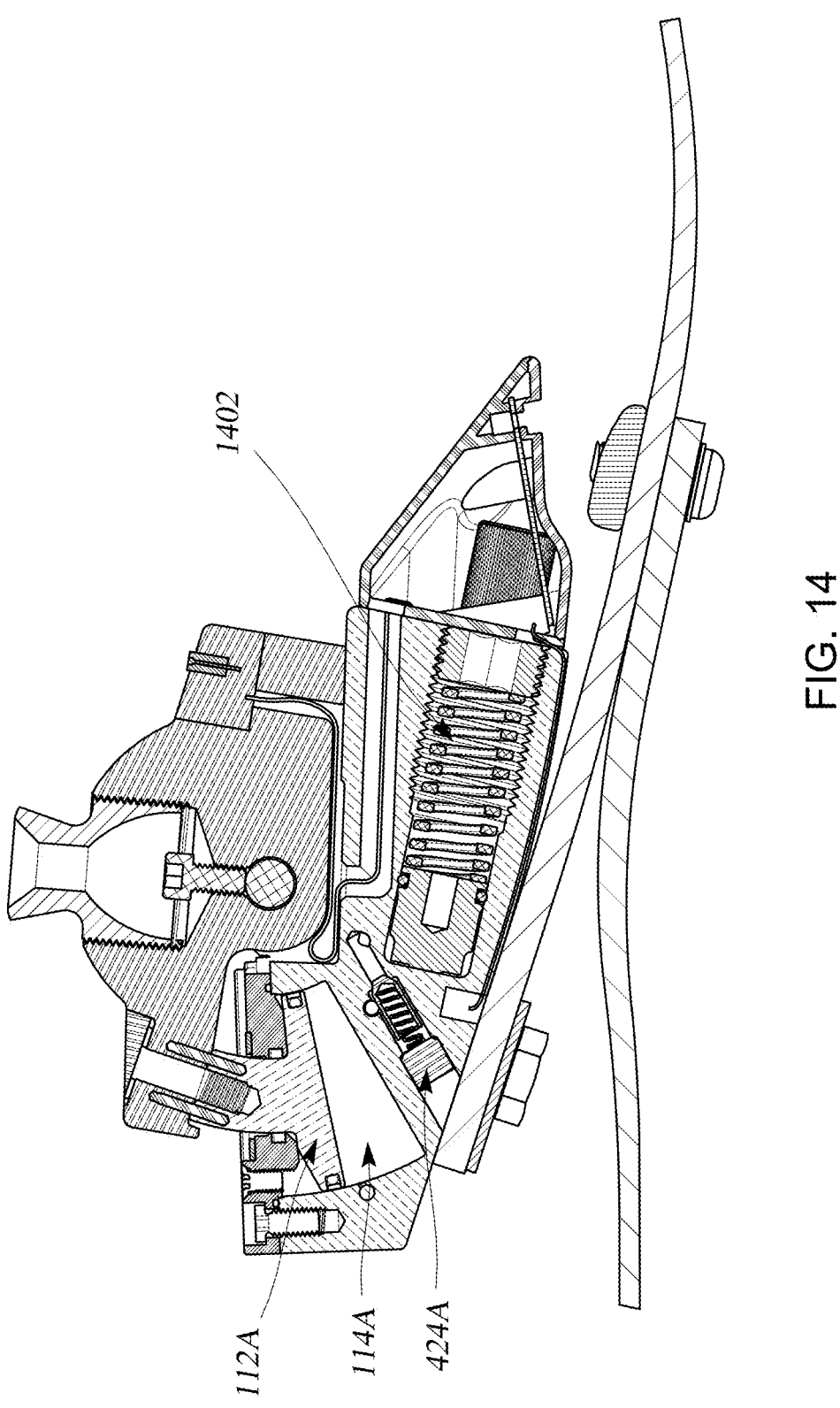
FIG. 14 illustrates a schematic partial cross-sectional view of an embodiment of a prosthetic or an orthotic device with a hydraulic prosthetic ankle with an accumulator.
Figure 15:
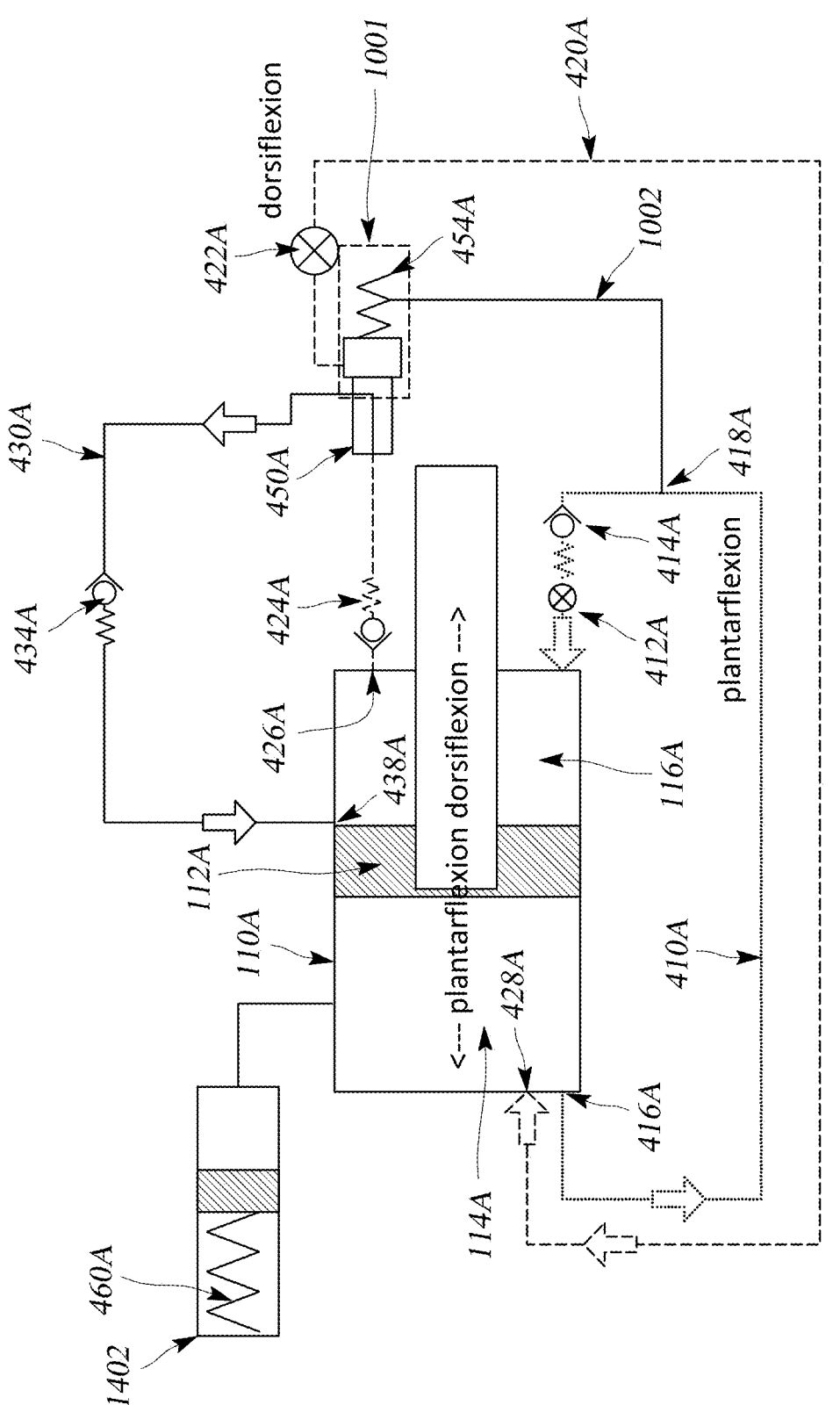
FIG. 15 schematically illustrates operation of an embodiment of a hydraulic prosthetic ankle during different phases of gait.

FIG. 14 shows a schematic partial cross-sectional view of another embodiment of the hydraulic prosthetic ankle 100A, further including an accumulator 1402. FIG. 15 schematically illustrates a hydraulic system 400A of the embodiment of the hydraulic prosthetic ankle 100A depicted in FIG. 14. The accumulator 1402 may be in fluid communication with one side of the cylinder 110A (e.g., with the first chamber 114A). The accumulator 1402 can include an elastic element 460A (e.g., spring, coil spring) that biases a piston of the accumulator 1402 toward delivering fluid to the first chamber 114A. When the hydraulic system 400A moves in plantarflexion, the volume within the cylinder 110A (e.g., in the first chamber 114A) would be reduced, pressurizing the accumulator 1402 (e.g., and compressing the elastic element or spring 460A). The pressure within the accumulator 1402 then provides a bias towards dorsiflexion.

During dorsiflexion motion of the prosthetic device 10A (e.g., movement of the piston 112A toward the right in FIG. 15), when low pressure (e.g., pressure below a threshold amount, or rate of change of pressure below a certain threshold) is applied to the diverter valve 450A (e.g., as sensed by the actuator 454A) and the piston 112A is located to the right of the opening 438A, the diverter valve 450A would be shifted towards the left side of the schematic illustration, connecting a pathway which would allow fluid to flow from the second chamber 116A of the cylinder 110A along the third passage 430A via the second check valve 424A, then the diverter valve 450A and then the third check valve 434A to the opening 438A to pass into the first chamber 114. The hydraulic system 400A may further include a drain passageway 1002 connecting a chamber 1001 near the diverter valve 450A to the first passage 410A.

In operation, as the piston 112A moves during dorsiflexion of the prosthetic device 10A, the hydraulic pressure within the second chamber 116A and around the opening 426A can increase during the earlier portion of the dorsiflexion (e.g., following transition from plantarflexion to dorsiflexion). The increase of the hydraulic pressure can be caused by the hydraulic dampening resistance of the second passage 420A and the downward movement (or rightward movement in the schematic illustration shown in FIG. 15) of the piston 112A corresponding to the forward rotation of the prosthetic ankle 100 relative to the foot portion 20A. However, as the piston 112A continues to move downward during dorsiflexion, the movement of the piston 112A can slow down (e.g., as the rotation of the ankle 100A relative to the foot 20A slows down when approaching the end of dorsiflexion and toe off), which can cause the hydraulic pressure to decrease. Additionally, the slowing down of the piston 112A during dorsiflexion can decrease the rate of change of the hydraulic pressure. Such decrease in the hydraulic pressure or in the rate of change of the hydraulic pressure during dorsiflexion can be used to determine when to change the position of the diverter valve 450A and trigger non-resistance flow (e.g., flow along third passage 430A of the hydraulic fluid between the second chamber 116A and the first chamber 114A.

As discussed above in connection with FIGS. 6 and 10, once the flow is diverted to the third passage 430A, because the third passage 430A provides no or negligible hydraulic resistance, the hydraulic fluid of the hydraulic system 400A can easily flow from the second chamber 116A to the first chamber 114A (without resistance) via the third passage 430A. The non-restricted (that is, with no or negligible hydraulic resistance) flow of the hydraulic fluid from the second chamber 116A to the first chamber 114A can eliminate or reduce the hydraulic resistance generated by the hydraulic system 400A and allow the piston 112A to move towards the maximum-dorsiflexion position (that is, the rightmost end of the hydraulic cylinder 110A shown in FIG. 10) with more ease due to the force exerted by the accumulator 1402 on the piston 112A. In some implementations, the restoring force exerted by the accumulator 1402 can further aid the movement of the piston 112A towards the maximum-dorsiflexion position (e.g. toe-up position) during the swing phase.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment may be used with a different embodiment described herein and the combination still fall within the scope of the disclosure. It should be understood that various features and aspects of the disclosed embodiments may be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations, one or more features from a claimed combination may, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described may be incorporated in the example methods and processes. For example, one or more additional operations may be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems may generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "may," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic ankle, the prosthetic ankle comprising:
a hydraulic cylinder, the hydraulic cylinder comprising a first chamber, a second chamber, and a piston separating the first chamber and the second chamber, the first chamber and the second chamber filled with a hydraulic fluid;
a first valve disposed along a first passage, the first passage and the first valve allowing dampened fluid flow between the first chamber and the second chamber during plantarflexion;
a second valve disposed along a second passage, the second passage and the second valve allowing dampened fluid flow between the first chamber and the second chamber during dorsiflexion; and
a diverter valve being in selective communication with the second passage and a third passage, a third valve disposed along the third passage, the third passage and the third valve allowing flow between the first chamber and the second chamber during dorsiflexion in a swing phase of gait, wherein a dampening resistance on the flow through the third passage is lower than a dampening resistance on the flow through the second passage,
wherein the diverter valve diverts the flow from the second passage to the third passage based on a system status.

2. The prosthetic ankle of claim 1, further comprising a spring disposed in the hydraulic cylinder and operatively coupled to the piston, the spring configured to impart a force on the piston during swing phase to dorsiflex a prosthetic foot coupled to the prosthetic ankle to lift a toe of the foot.

3. The prosthetic ankle of claim 1, wherein the third passage and the third valve allow non-restrictive flow between the first chamber and the second chamber.

4. The prosthetic ankle of claim 1, wherein the system status comprises a pressure threshold amount.

5. The prosthetic ankle of claim 1, wherein the system status comprises a degree of dorsiflexion.

6. The prosthetic ankle of claim 1, wherein the system status comprises an indication of toe off.

7. The prosthetic ankle of claim 1, further comprising an accumulator in fluid communication with the hydraulic cylinder, wherein hydraulic fluid is pressurized in the accumulator during plantarflexion and the pressurized hydraulic fluid in the accumulator applies a biasing force on the piston toward dorsiflexion.

8. The prosthetic ankle of claim 1, further comprising a drain passage between the diverter valve and the first passage.

9. A prosthetic device comprising:
a foot portion; and
an ankle portion coupled to the foot portion, the ankle portion comprising:
a hydraulic cylinder, the hydraulic cylinder comprising a first chamber, a second chamber, and a piston separating the first chamber and the second chamber, the first chamber and the second chamber filled with a hydraulic fluid, a first valve disposed along a first passage, the first passage and the first valve allowing dampened fluid flow between the first chamber and the second chamber during plantarflexion, a second valve disposed along a second passage, the second passage and the second valve allowing dampened fluid flow between the first chamber and the second chamber during dorsiflexion, and a diverter valve being in selective communication with the second passage and a third passage, a third valve disposed along the third passage, the third passage and the third valve allowing flow between the first chamber and the second chamber during dorsiflexion in a swing phase of gait, wherein a dampening resistance on the flow through the third passage is lower than a dampening resistance on the flow through the second passage, wherein the diverter valve diverts the flow from the second passage to the third passage based on a system status, and wherein an orientation of a top portion of the ankle portion is configured to change based at least in part on a position of the piston within the hydraulic cylinder.

10. The prosthetic device of claim 9, further comprising a spring disposed in the hydraulic cylinder and operatively coupled to the piston, the spring configured to impart a force on the piston during swing phase to dorsiflex the foot portion to lift a toe of the foot portion.

11. The prosthetic device of claim 9, wherein the third passage and third valve allow non-restrictive flow between the first chamber and the second chamber.

12. The prosthetic device of claim 9, wherein the system status comprises a pressure threshold amount.

13. The prosthetic device of claim 9, wherein the system status comprises a degree of dorsiflexion.

14. The prosthetic device of claim 9, wherein the system status comprises an indication of toe off.

15. The prosthetic device of claim 9, further comprising an accumulator in fluid communication with the hydraulic cylinder, wherein hydraulic fluid is pressurized in the accumulator during plantarflexion and the pressurized hydraulic fluid in the accumulator applies a biasing force on the piston toward dorsiflexion.

16. The prosthetic device of claim 9, further comprising a drain passage between the diverter valve and the first passage.

\* \* \* \* \*